United States Patent
Cote et al.

(10) Patent No.: US 11,229,753 B2
(45) Date of Patent: Jan. 25, 2022

(54) SUBCUTANEOUS INSERTION SYSTEMS, DEVICES AND RELATED METHODS

(71) Applicant: Smiths Medical ASD, Inc., Plymouth, MN (US)

(72) Inventors: Steven Albert Cote, Stillwater, MN (US); Mark Henry Faust, Lino Lakes, MN (US); David Andrae Justmann, Somerset, WI (US)

(73) Assignee: Smiths Medical ASD, Inc., Plymouth, MN (US)

( * ) Notice: Subject to any disclaimer, the term of this patent is extended or adjusted under 35 U.S.C. 154(b) by 203 days.

(21) Appl. No.: 16/097,449

(22) PCT Filed: Apr. 25, 2017

(86) PCT No.: PCT/US2017/029353
§ 371 (c)(1),
(2) Date: Oct. 29, 2018

(87) PCT Pub. No.: WO2017/189541
PCT Pub. Date: Nov. 2, 2017

(65) Prior Publication Data
US 2019/0151567 A1    May 23, 2019

Related U.S. Application Data

(60) Provisional application No. 62/329,352, filed on Apr. 29, 2016.

(51) Int. Cl.
*A61M 5/32* (2006.01)
*A61B 5/00* (2006.01)
(Continued)

(52) U.S. Cl.
CPC .......... *A61M 5/3287* (2013.01); *A61B 5/002* (2013.01); *A61B 5/6848* (2013.01);
(Continued)

(58) Field of Classification Search
CPC .......... A61M 5/158; A61M 2025/0286; A61M 2039/0273; A61M 25/02; A61M 38/0247;
(Continued)

(56) References Cited

U.S. PATENT DOCUMENTS 3,094,989 A   6/1963 Stauffer
3,547,119 A   12/1970 Hall et al.
(Continued)

FOREIGN PATENT DOCUMENTS

AU   2004289184 B2   11/2010
AU   2005264927 B2   3/2011
(Continued)

OTHER PUBLICATIONS

Communication dated Dec. 10, 2019 for EP Application No. 17790248.3, 8 pages.
(Continued)

*Primary Examiner* — Scott J Medway
(74) *Attorney, Agent, or Firm* — Patterson Thuente Pederson, P.A.

(57) ABSTRACT

Embodiments relate to subcutaneous insertion systems comprising a surface device to be applied to a patient's skin and an insertion system for applying the surface device to the patient, wherein the applying can include subcutaneous insertion of a cannula or other element, and related devices and methods. The surface device comprises a surface for application to the skin of a patient and a subcutaneous element, such as a cannula, wire, filament or other device, extending from the skin's surface at an angle greater than 0 degrees and less than 90 degrees.

21 Claims, 20 Drawing Sheets

(51) Int. Cl.
*A61M 5/142* (2006.01)
*A61M 25/06* (2006.01)
*A61M 5/158* (2006.01)
*A61B 5/145* (2006.01)
*A61M 5/172* (2006.01)
*A61B 17/34* (2006.01)
*A61M 5/46* (2006.01)

(52) U.S. Cl.
CPC ....... *A61B 5/6861* (2013.01); *A61M 5/14248* (2013.01); *A61M 5/158* (2013.01); *A61M 25/06* (2013.01); *A61B 5/0084* (2013.01); *A61B 5/14532* (2013.01); *A61B 5/14542* (2013.01); *A61B 5/6865* (2013.01); *A61B 17/3403* (2013.01); *A61B 2562/162* (2013.01); *A61M 5/46* (2013.01); *A61M 2005/1585* (2013.01); *A61M 2005/1587* (2013.01); *A61M 2005/1726* (2013.01); *A61M 2205/3576* (2013.01)

(58) Field of Classification Search
CPC .... A61M 5/14276; A61M 5/427; A61M 5/46; A61M 2005/1585; A61M 2005/1581; A61M 2005/1587; A61M 5/14248; A61M 2005/14252; A61M 2039/027; A61M 39/02; A61B 5/14532; A61B 5/1411
See application file for complete search history.

(56) References Cited

U.S. PATENT DOCUMENTS

| | | |
|---|---|---|
| 4,235,234 A | 11/1980 | Whitney et al. |
| 4,378,015 A | 3/1983 | Wardlaw |
| 4,531,937 A | 7/1985 | Yates |
| 4,563,177 A | 1/1986 | Kamen |
| 4,645,495 A | 2/1987 | Vaillancourt |
| 4,747,831 A | 5/1988 | Kulli |
| 4,755,173 A | 7/1988 | Konopka et al. |
| 4,781,695 A * | 11/1988 | Dalton ............... A61M 39/0208 604/175 |
| 4,805,791 A | 2/1989 | Begley |
| 4,813,939 A | 3/1989 | Marcus |
| 4,994,042 A | 2/1991 | Vadher |
| 5,092,853 A | 3/1992 | Couvertier, II |
| 5,122,119 A | 6/1992 | Lucas |
| 5,129,884 A | 7/1992 | Dysarz |
| 5,135,496 A | 8/1992 | Vetter et al. |
| 5,135,502 A | 8/1992 | Koenig, Jr. et al. |
| 5,137,516 A | 8/1992 | Rand et al. |
| 5,167,632 A | 12/1992 | Eid et al. |
| 5,176,650 A | 1/1993 | Haining |
| 5,176,662 A | 1/1993 | Bartholomew et al. |
| 5,248,301 A | 9/1993 | Koenig, Jr. et al. |
| 5,257,980 A | 11/1993 | Van Antwerp et al. |
| 5,391,151 A | 2/1995 | Wilmot |
| 5,451,210 A | 9/1995 | Kramer et al. |
| 5,522,803 A | 6/1996 | Teissen-Simony |
| 5,545,143 A | 8/1996 | Fischell et al. |
| 5,573,510 A | 11/1996 | Isaacson |
| 5,575,777 A | 11/1996 | Cover et al. |
| 5,584,813 A | 12/1996 | Livingston et al. |
| 5,591,188 A | 1/1997 | Waisman |
| 5,676,156 A | 10/1997 | Yoon |
| 5,738,641 A | 4/1998 | Watson et al. |
| 5,817,058 A | 10/1998 | Shaw |
| 5,833,666 A | 11/1998 | Davis et al. |
| 5,848,989 A | 12/1998 | Villani |
| 5,848,990 A | 12/1998 | Cirelli et al. |
| 5,851,197 A | 12/1998 | Marano et al. |
| 5,865,842 A | 2/1999 | Knuth et al. |
| 5,873,856 A | 2/1999 | Hjertman et al. |
| 5,947,931 A | 9/1999 | Bierman |
| 5,954,643 A | 9/1999 | Van Antwerp et al. |
| 5,968,011 A | 10/1999 | Larsen et al. |
| 5,971,950 A | 10/1999 | Lopez et al. |
| 5,980,506 A | 11/1999 | Mathiasen |
| 6,017,328 A | 1/2000 | Fischell et al. |
| 6,056,718 A | 5/2000 | Funderburk et al. |
| 6,056,726 A | 5/2000 | Isaacson |
| 6,074,369 A | 6/2000 | Sage et al. |
| 6,077,244 A | 6/2000 | Botich et al. |
| 6,086,575 A | 7/2000 | Mejslov |
| 6,093,172 A | 7/2000 | Funderburk et al. |
| 6,123,690 A | 9/2000 | Mejslov |
| 6,159,181 A | 12/2000 | Crossman et al. |
| 6,191,338 B1 | 2/2001 | Haller |
| 6,293,925 B1 | 9/2001 | Safabash et al. |
| 6,302,866 B1 | 10/2001 | Marggi |
| 6,355,021 B1 | 3/2002 | Nielson et al. |
| 6,419,699 B1 | 7/2002 | Schuessler |
| 6,428,515 B1 | 8/2002 | Bierman et al. |
| 6,447,482 B1 | 9/2002 | Ronborg et al. |
| 6,450,992 B1 | 9/2002 | Cassidy, Jr. |
| 6,517,517 B1 | 2/2003 | Farrugia et al. |
| 6,520,938 B1 | 2/2003 | Funderburk et al. |
| 6,549,810 B1 | 4/2003 | Leonard et al. |
| 6,572,586 B1 | 6/2003 | Wojcik |
| 6,579,267 B2 | 6/2003 | Lynch et al. |
| 6,607,509 B2 | 8/2003 | Bobroff et al. |
| 6,613,064 B2 | 9/2003 | Rutynowski et al. |
| 6,620,136 B1 | 9/2003 | Pressly, Sr. et al. |
| 6,685,674 B2 | 2/2004 | Douglas et al. |
| 6,736,797 B1 | 5/2004 | Larsen et al. |
| 6,749,589 B1 | 6/2004 | Douglas et al. |
| 6,830,562 B2 | 12/2004 | Mogensen et al. |
| 6,923,791 B2 | 8/2005 | Douglas |
| 6,926,694 B2 | 8/2005 | Morano-Ford et al. |
| 6,991,620 B2 | 1/2006 | Marano-Ford et al. |
| 7,018,344 B2 | 3/2006 | Bressler et al. |
| 7,022,108 B2 | 4/2006 | Marano-Ford et al. |
| 7,052,483 B2 | 5/2006 | Wojcik |
| 7,056,302 B2 | 6/2006 | Douglas |
| 7,129,389 B1 | 10/2006 | Watson |
| 7,297,138 B2 | 11/2007 | Fangrow, Jr. |
| 7,303,543 B1 | 12/2007 | Maule et al. |
| 7,407,493 B2 | 8/2008 | Cane' |
| D576,267 S | 9/2008 | Mogensen et al. |
| 7,520,867 B2 | 4/2009 | Bowman et al. |
| 7,585,287 B2 | 9/2009 | Bresina et al. |
| 7,594,902 B2 * | 9/2009 | Horisberger .......... A61M 5/158 604/288.01 |
| 7,699,807 B2 | 4/2010 | Faust et al. |
| 7,699,808 B2 | 4/2010 | Marrs et al. |
| 7,731,691 B2 | 6/2010 | Cote et al. |
| 7,850,658 B2 | 12/2010 | Faust et al. |
| 7,879,010 B2 | 2/2011 | Hunn et al. |
| 7,931,615 B2 | 4/2011 | Fangrow, Jr. |
| 7,985,199 B2 * | 7/2011 | Kornerup ............... A61M 5/158 604/93.01 |
| 7,993,306 B2 | 8/2011 | Marrs et al. |
| 8,152,769 B2 | 4/2012 | Douglas et al. |
| 8,157,773 B2 * | 4/2012 | Tashjian ................ A61M 5/158 604/244 |
| 8,226,614 B2 * | 7/2012 | Turner ............... A61M 5/16804 604/164.04 |
| 8,303,545 B2 * | 11/2012 | Schraga ................ A61M 5/158 604/167.02 |
| 8,317,759 B2 | 11/2012 | Moberg et al. |
| 8,343,115 B2 | 1/2013 | Lynch et al. |
| 8,795,309 B2 | 8/2014 | Lacy |
| 9,192,717 B2 | 11/2015 | Cote et al. |
| 9,227,013 B2 | 1/2016 | Lacy |
| 9,662,440 B2 * | 5/2017 | Yodfat ................ A61M 5/1424 |
| 9,795,777 B2 * | 10/2017 | Sonderegger ...... A61M 39/1055 |
| 9,993,595 B2 | 6/2018 | Michaud et al. |
| 10,076,606 B2 * | 9/2018 | Ambruzs ............. A61M 5/158 |
| 10,307,532 B2 * | 6/2019 | Pearson ................ A61M 39/02 |
| 10,434,285 B2 * | 10/2019 | Schoonmaker ....... A61M 5/158 |
| 2001/0039387 A1 | 11/2001 | Rutynowski et al. |
| 2001/0053889 A1 * | 12/2001 | Marggi ............... A61M 25/0612 604/164.11 |
| 2002/0010423 A1 | 1/2002 | Gross et al. |

(56) References Cited

U.S. PATENT DOCUMENTS

| | | |
|---|---|---|
| 2002/0022855 A1 | 2/2002 | Bobroff et al. |
| 2002/0045867 A1 | 4/2002 | Nielson et al. |
| 2002/0072720 A1* | 6/2002 | Hague .......... A61M 5/158 |
| | | 604/264 |
| 2002/0077599 A1 | 6/2002 | Wojcik |
| 2002/0082543 A1 | 6/2002 | Park et al. |
| 2002/0123724 A1 | 9/2002 | Douglas et al. |
| 2002/0123740 A1 | 9/2002 | Flaherty et al. |
| 2002/0161332 A1 | 10/2002 | Ramey |
| 2002/0173769 A1 | 11/2002 | Gray et al. |
| 2003/0014018 A1 | 1/2003 | Giambattista et al. |
| 2003/0060776 A1 | 3/2003 | Heiniger |
| 2003/0060781 A1 | 3/2003 | Mogensen et al. |
| 2003/0060798 A1 | 3/2003 | Fischer et al. |
| 2003/0109829 A1 | 6/2003 | Mogensen et al. |
| 2003/0125669 A1 | 7/2003 | Safabash et al. |
| 2003/0130619 A1 | 7/2003 | Safabash et al. |
| 2003/0158520 A1 | 8/2003 | Safabash et al. |
| 2003/0181863 A1* | 9/2003 | Ackley .......... A61M 37/0015 |
| | | 604/201 |
| 2003/0199823 A1 | 10/2003 | Bobroff et al. |
| 2003/0225373 A1 | 12/2003 | Bobroff et al. |
| 2003/0225374 A1 | 12/2003 | Mathiasen |
| 2003/0236498 A1 | 12/2003 | Gross et al. |
| 2004/0002682 A1 | 1/2004 | Kovelman et al. |
| 2004/0116866 A1 | 6/2004 | Gorman et al. |
| 2004/0138612 A1 | 7/2004 | Shermer et al. |
| 2004/0143216 A1 | 7/2004 | Douglas et al. |
| 2004/0147877 A1 | 7/2004 | Heuser |
| 2004/0158207 A1 | 8/2004 | Hunn et al. |
| 2004/0162521 A1 | 8/2004 | Bengtsson |
| 2004/0199123 A1 | 10/2004 | Nielsen |
| 2004/0204687 A1 | 10/2004 | Mogensen et al. |
| 2004/0215151 A1 | 10/2004 | Marshall et al. |
| 2004/0236284 A1 | 11/2004 | Hoste et al. |
| 2004/0260250 A1 | 12/2004 | Harris et al. |
| 2005/0043687 A1 | 2/2005 | Mogensen et al. |
| 2005/0075606 A1 | 4/2005 | Botich et al. |
| 2005/0090779 A1 | 4/2005 | Osypka |
| 2005/0101910 A1 | 5/2005 | Bowman et al. |
| 2005/0101912 A1 | 5/2005 | Faust et al. |
| 2005/0101932 A1 | 5/2005 | Cote et al. |
| 2005/0101933 A1 | 5/2005 | Marrs |
| 2005/0107743 A1 | 5/2005 | Fangrow, Jr. |
| 2005/0113761 A1 | 5/2005 | Faust et al. |
| 2005/0119611 A1 | 6/2005 | Marano-Ford et al. |
| 2005/0131346 A1 | 6/2005 | Douglas |
| 2005/0215979 A1 | 9/2005 | Kornerup et al. |
| 2005/0240154 A1* | 10/2005 | Mogensen .......... A61M 5/158 |
| | | 604/173 |
| 2005/0283114 A1 | 12/2005 | Bresina et al. |
| 2006/0041224 A1 | 2/2006 | Jensen |
| 2006/0129090 A1 | 6/2006 | Moberg et al. |
| 2006/0173413 A1 | 8/2006 | Fangrow |
| 2007/0066955 A1* | 3/2007 | Sparholt .......... A61J 1/1406 |
| | | 604/415 |
| 2007/0142776 A9 | 6/2007 | Kovelman et al. |
| 2007/0276355 A1* | 11/2007 | Nielsen .......... A61M 39/04 |
| | | 604/533 |
| 2008/0071156 A1 | 3/2008 | Brister et al. |
| 2008/0103450 A1 | 5/2008 | Marrs et al. |
| 2008/0154205 A1 | 6/2008 | Wojcik |
| 2008/0243051 A1 | 10/2008 | DeStefano |
| 2009/0012472 A1* | 1/2009 | Ahm .......... A61M 5/158 |
| | | 604/138 |
| 2009/0076453 A1* | 3/2009 | Mejlhede .......... A61M 5/158 |
| | | 604/151 |
| 2009/0124979 A1 | 5/2009 | Raymond et al. |
| 2009/0143763 A1* | 6/2009 | Wyss .......... A61M 5/158 |
| | | 604/506 |
| 2009/0215979 A1 | 8/2009 | Dorwald |
| 2009/0216215 A1 | 8/2009 | Thalmann et al. |
| 2009/0264825 A1 | 10/2009 | Cote et al. |
| 2009/0287153 A1 | 11/2009 | Bresina et al. |
| 2010/0049129 A1 | 2/2010 | Yokoi et al. |
| 2010/0063453 A1* | 3/2010 | Theander .......... A61M 5/158 |
| | | 604/180 |
| 2010/0217105 A1 | 8/2010 | Yodfat et al. |
| 2011/0028982 A1 | 2/2011 | Lacy |
| 2011/0125106 A1 | 5/2011 | Giambattista et al. |
| 2012/0179106 A1 | 7/2012 | Cote et al. |
| 2013/0012881 A1 | 1/2013 | Lacy |
| 2013/0274576 A1* | 10/2013 | Amirouche .......... A61B 5/14503 |
| | | 600/365 |
| 2014/0039453 A1 | 2/2014 | Sonderegger |
| 2014/0088555 A1* | 3/2014 | Li .......... A61M 5/172 |
| | | 604/506 |
| 2016/0296695 A1 | 10/2016 | Hassaman et al. |
| 2016/0339172 A1 | 11/2016 | Michaud et al. |

FOREIGN PATENT DOCUMENTS

| | | |
|---|---|---|
| AU | 2004289183 B2 | 4/2011 |
| AU | 2004289185 A1 | 6/2011 |
| CA | 1272423 A | 8/1990 |
| CA | 2446976 C | 1/2002 |
| CA | 2544293 C | 1/2012 |
| CA | 2544303 C | 6/2013 |
| CA | 2570868 C | 5/2014 |
| CA | 2544299 C | 1/2016 |
| CA | 2792489 C | 3/2016 |
| CN | 100506310 C | 7/2009 |
| CN | 100571799 C | 12/2009 |
| CN | 101018578 B | 4/2010 |
| CN | 1878592 B | 7/2011 |
| DE | 29905072 U1 | 9/1999 |
| DE | 20220543 U1 | 10/2003 |
| EP | 0397951 B1 | 5/1989 |
| EP | 0239244 B1 | 9/1991 |
| EP | 0451040 A1 | 10/1991 |
| EP | 0290176 B1 | 2/1996 |
| EP | 0615768 B1 | 12/1999 |
| EP | 1329233 B1 | 9/2004 |
| EP | 1687046 B1 | 9/2008 |
| EP | 2380620 A2 | 10/2011 |
| EP | 2383011 A2 | 11/2011 |
| EP | 1789116 B1 | 5/2013 |
| EP | 2596821 A1 | 5/2013 |
| EP | 1691877 B1 | 12/2013 |
| EP | 1684840 B1 | 10/2017 |
| FR | 2752164 A1 | 2/1998 |
| JP | H 11-347120 A | 12/1999 |
| JP | 2000-254225 A | 9/2000 |
| JP | 2004-524926 A | 8/2004 |
| JP | 2007-510497 A | 4/2007 |
| JP | 4685024 B2 | 5/2011 |
| JP | 4891086 B2 | 12/2011 |
| JP | 2013-039416 A | 2/2013 |
| JP | 5575084 B2 | 8/2014 |
| JP | 5976091 B2 | 7/2016 |
| WO | WO 1996/032981 A1 | 10/1996 |
| WO | WO 1998/058693 A1 | 12/1998 |
| WO | WO 1999/034739 A1 | 7/1999 |
| WO | WO 1999/033504 A9 | 11/1999 |
| WO | WO 2002/081012 A3 | 10/2002 |
| WO | WO 2002/083206 A2 | 10/2002 |
| WO | WO 2002/100457 A3 | 12/2002 |
| WO | WO 2002/100467 A2 | 12/2002 |
| WO | WO 2002/102442 A1 | 12/2002 |
| WO | WO 2004/101071 A3 | 11/2004 |
| WO | WO 2005/046767 A1 | 5/2005 |
| WO | WO 2005/046780 A1 | 5/2005 |
| WO | WO 2005/046781 A1 | 5/2005 |
| WO | WO 2005/049117 A2 | 6/2005 |
| WO | WO 2006/009665 A1 | 1/2006 |
| WO | WO 2006/020851 A1 | 2/2006 |
| WO | WO 2008/022476 A1 | 2/2010 |
| WO | WO 2011/014492 A1 | 2/2011 |

(56) References Cited

OTHER PUBLICATIONS

FreeStyle Libre https://www.freestylelibre.us/support/overview.html Getting Started introduction video. © 2018 Abbott Laboratories.
International Search Report for corresponding International Application No. PCT/US2017/029353 dated Aug. 3, 2017; 12 pages.
Written Opinion of the International Searching Authority for corresponding International Application No. PCT/US2017/029353 dated Aug. 3, 2017; 10 pages.
"Technical Information Sheet Product No. 1538L, 3M™ Medical Rayon Woven Tape on Liner," 3M, 2 pages (2003).
Inset®Visual Guide, Unomedical, 16 pages, 2004.
Smiths Medical MD, Inc., "Infusion Sets Overview," 2009, 2 pages.
Mike H., "New FreeStyle Libre 'Hybrid' Glucose Monitor Approved in Europe," Sep. 5, 2014, 6 paegs.
Application and File history for U.S. Appl. No. 10/705,719, filed Nov. 10, 2003. Inventors: Cote et al.
Application and File history for U.S. Appl. No. 10/705,725, filed Nov. 10, 2003. Inventors: Faust et al.
Application and File history for U.S. Appl. No. 10/705,736, filed Apr. 20, 2010, Inventors: Marrs et al.
Application and File history for U.S. Appl. No. 10/869,181, filed Jun. 16, 2004. Inventors: Bresina et al.
Application and File history for U.S. Appl. No. 10/918,212, filed Dec. 14, 2010. Inventors: Faust et al.
Application and File history for U.S. Appl. No. 11/554,835, filed Oct. 31, 2006. Inventors: Marrs et al.
Application and File history for U.S. Appl. No. 12/509,063, filed Jul. 24, 2009. Inventors: Bresina et al.
Application and File history for U.S. Appl. No. 12/844,402, filed Jul. 27, 2010, Inventors: Lacy.
Application and File history for U.S. Appl. No. 13/351,993, filed Jan. 17, 2012. Inventors: Cote et al.
Application and File history for U.S. Appl. No. 13/619,396, filed Sep. 14, 2012, Inventors: Lacy.
Transcript of Diabetando Diabetando YouTube video "FreeStyle Libre Getting Start," https://www.youtube.com/watch?v=OcXwO9YBJxE, Sep. 2, 2014, 39 pages.

* cited by examiner

SECTION A-A

SUBCUTANEOUS INSERTION SYSTEMS, DEVICES AND RELATED METHODS

CROSS-REFERENCE TO RELATED APPLICATIONS

The present application is a National Phase entry of PCT Application No. PCT/US2017/029353, filed on Apr. 25, 2017, which claims priority to U.S. Provisional Patent Application No. 62/329,352, filed on Apr. 29, 2016, which are hereby fully incorporated herein by reference.

TECHNICAL FIELD

Embodiments relate generally to medical devices, and more particularly to subcutaneous insertion systems comprising a device to be applied to a patient and an insertion system for applying the device to the patient, wherein the applying can include subcutaneous insertion of a cannula or other element, and related devices and methods.

BACKGROUND

A variety of devices can be applied to a patient to provide a treatment or monitor a patient condition. Some can do both. One example is an infusion system used to deliver substances such as fluids and medications into the subcutaneous layer of skin of a patient. Typically, a subcutaneous infusion system includes a site applied to the surface of the skin of a patient, the site having a cannula that is introduced into the skin, as well as a tube extending from the site to, for example, an infusion pump to deliver the substance. Another example is a patient monitoring system used to check or monitor one or more conditions of a patient (e.g., blood levels, such as glucose or oxygen), which also can include a device applied to the skin of the patient and comprising a cannula, filament, wire or other device introduced at least partially subcutaneously. For convenience, surface devices generally, whether for infusion, monitoring or some other purpose, will generally be referred to herein as sites. In some embodiments, sites refer to sensors or "patch pumps".

In current designs, it is typically necessary to introduce the cannula or other device of the site into the skin of the patient while maintaining the site at a given orientation. The orientation of the cannula is also fixed, extending perpendicularly from a bottom surface of the site and therefore inserted straight into, or perpendicularly to, the surface of the skin. While this perpendicular orientation can require a shorter cannula and a shorter needle for insertion of the cannula while also being easy and convenient for user self-application using an insertion aid device, perpendicular insertion can be inconvenient for some users, such as those with low body fat or who are active and desire a more secure placement of the infusion device and cannula. Additionally, some users may wish to control the angle of insertion of the cannula, depending on location and anatomy, to increase comfort and placement efficacy. Still others may find the perpendicular orientation difficult to administer when applying the site to some locations on the body.

In addition, devices for assisting in insertion of the cannula of an infusion device into the skin of the patient are known. For example, some devices utilize springs to automatically drive a needle into the skin of a patient to introduce the cannula of the site into the subcutaneous layer. Because a needle is used to introduce the cannula of the infusion device into the subcutaneous layer of skin, there is a risk associated with inadvertent exposure to the needle. Further, patients may react adversely to viewing the needle prior to insertion and may, for example, be reluctant to self-insert the needle into the skin. Prior devices may not adequately shroud the needle prior to and/or after introduction of the site.

Other issues of concern in the design and use of insertion devices include ease of use by the patient and sterility. For example, some patients may have difficulty loading an infusion device into an insertion device.

It is therefore desirable to provide new designs for subcutaneous inserter devices and other devices used to assist in the introduction of a device into the skin of a patient.

SUMMARY

Embodiments described or otherwise contemplated herein substantially meet the aforementioned needs; for example, an insertion device comprising a housing comprising a first end; a sleeve slidably arranged at least partially in the housing; a cylinder hub at least partially arranged in the sleeve and the housing and comprising a shoulder portion and a body portion, the shoulder portion proximate to the first end of the housing; a needle hub slidably arranged in the cylinder hub and comprising a needle; and a site comprising a patient side surface and a subcutaneous element, the subcutaneous element coupled to the site at an angle greater than 0 degrees and less than 90 degrees with respect to the patient side surface, the site arranged within the housing such that the needle can pass through at least a portion of the site to enter the subcutaneous element at the angle.

In an embodiment, a method comprises providing an insertion device comprising a housing comprising a first end, a sleeve slidably arranged at least partially in the housing, a cylinder hub at least partially arranged in the sleeve and the housing and comprising a shoulder portion and a body portion, the shoulder portion proximate to the first end of the housing, and a needle hub slidably arranged in the cylinder hub and comprising a needle; providing a site to be applied by the insertion device, the site comprising a patient side surface and a subcutaneous element to be inserted by the insertion device, the subcutaneous element coupled to the site at an angle greater than 0 degrees and less than 90 degrees with respect to the patient side surface; and configuring the insertion device and the site to be coupled with one another such that the needle can pass through at least a portion of the site to enter the subcutaneous element at the angle to insert the subcutaneous element during use.

In an embodiment, an insertion device comprises a housing comprising a first end; a sleeve slidably arranged at least partially in the housing; a cylinder hub at least partially arranged in the sleeve and the housing and comprising a shoulder portion and a body portion, the shoulder portion proximate to the first end of the housing; and a needle hub slidably arranged in the cylinder hub and comprising a needle; wherein the insertion device is configured to be coupled with a site to insert a subcutaneous element of the site subcutaneously, the subcutaneous element coupled to the site at an angle greater than 0 degrees and less than 90 degrees with respect to a patient-contacting surface of the site, the site coupled with the insertion device such that the needle can pass through at least a portion of the site to enter the subcutaneous element at the angle.

The above summary is not necessarily intended to describe each illustrated embodiment or every implementation of the subject matter hereof. The figures and the detailed description that follow more particularly exemplify these embodiments.

BRIEF DESCRIPTION OF THE DRAWINGS

Subject matter hereof may be more completely understood in consideration of the following detailed description of various embodiments of the subject matter in connection with the accompanying drawings, in which.

Figure 1:
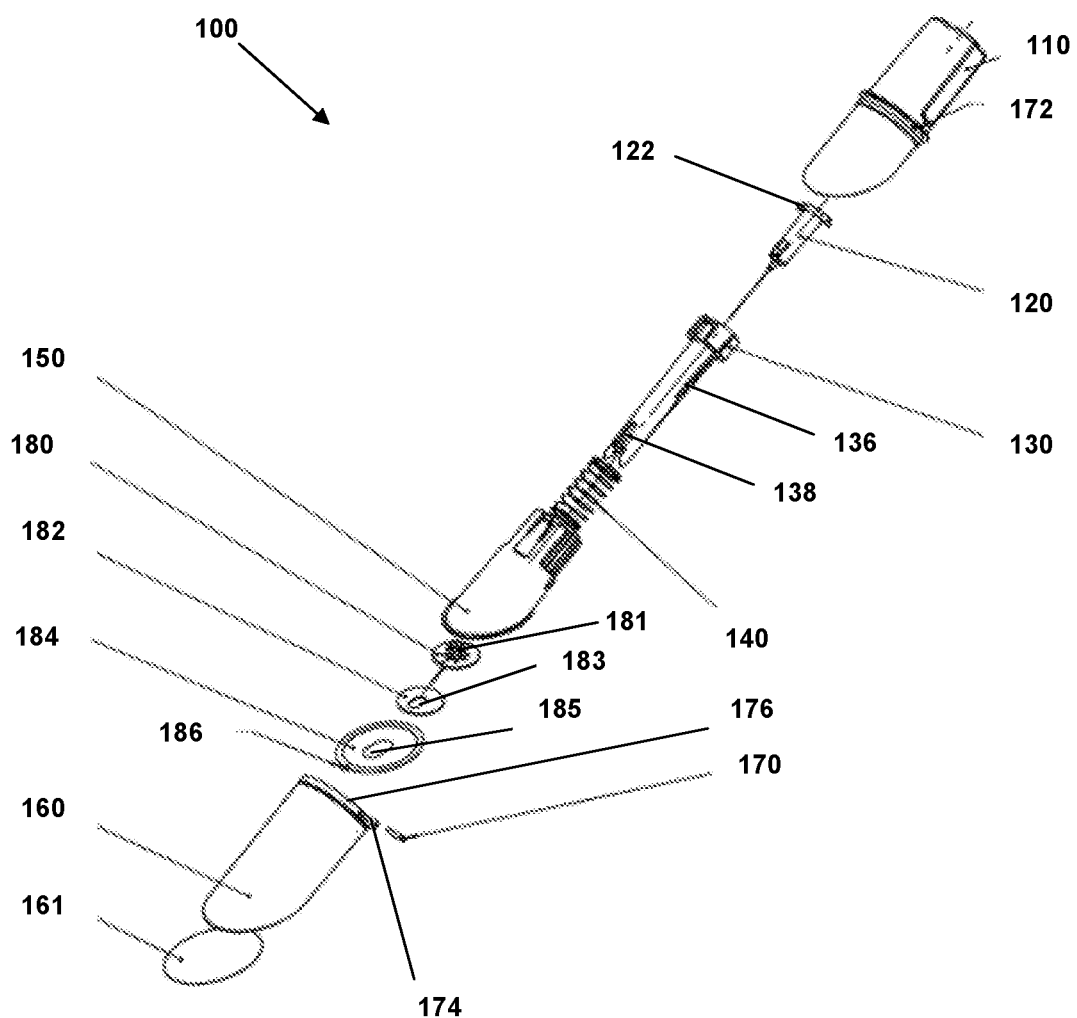
FIG. 1 is an exploded view of an insertion device according to an embodiment.
Figure 1A:
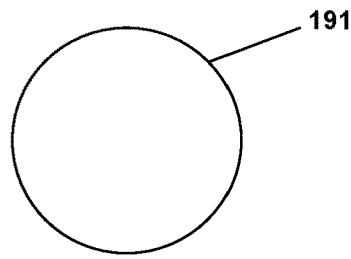
FIGS. 1A-H are perimeter shapes for sites, site pads, and sleeve pads according to various embodiments.
Figure 1B:
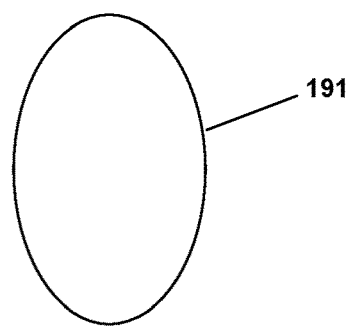
Figure 1C:
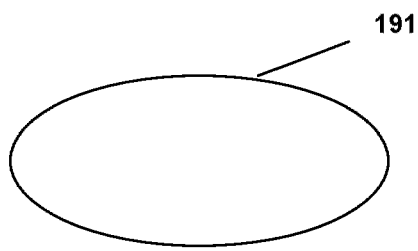
Figure 1D:
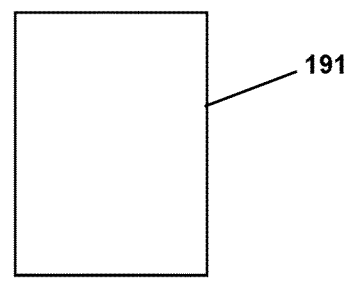
Figure 1E:
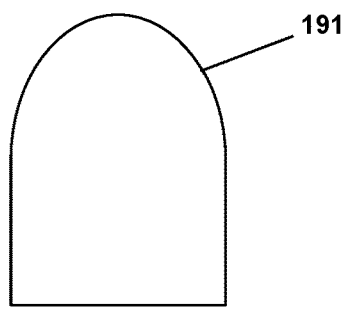
Figure 1F:
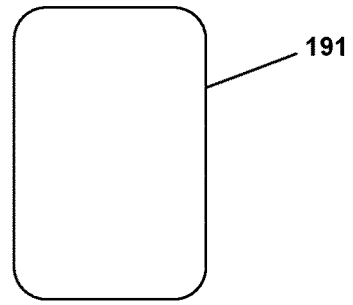
Figure 1G:
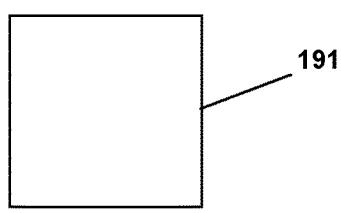
Figure 1H:
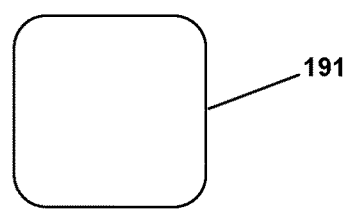

While embodiments are amenable to various modifications and alternative forms, specifics thereof have been shown by way of example in the drawings and will be described in detail. It should be understood, however, that the intention is not to limit subject matter hereof to the particular embodiments described. On the contrary, the intention is to cover all modifications, equivalents, and alternatives falling within the spirit and scope of subject matter hereof in accordance with the appended claims.

DETAILED DESCRIPTION

Embodiments relate to subcutaneous insertion systems comprising a site or other surface device to be applied to a patient and an insertion system for applying the site or other surface device to the patient, wherein the applying can include subcutaneous insertion of a cannula or other element, and related devices and methods. The site or other surface device can comprise a device applied to the skin of the patient and comprising a cannula, filament, wire, sensor or other subcutaneous element to be introduced at least partially subcutaneously into the skin of a patient. For convenience, sites and other surface devices generally, whether for infusion, monitoring or some other purpose, will generally be referred to herein as sites. In some embodiments, sites may refer to sensors or "patch pumps".

In an embodiment, a subcutaneous insertion system comprises a site and an insertion device for applying the site to the skin of a user. The site comprises a surface for application to the skin of a patient and a subcutaneous element, such as a cannula, filament, wire, sensor or other subcutaneous element to be introduced at least partially subcutaneously into the skin of a patient, extending from the surface at an angle greater than 0 degrees and less than 90 degrees. The site can be preloaded in the insertion device, which comprises a needle configured to interact with the cannula or other subcutaneous element to insert the cannula or other subcutaneous element into the skin of the patient at an angle greater than 0 degrees and less than 90 degrees with respect to the surface of the skin of the patient as the site is applied to the surface of the skin of the patient by the insertion device. The insertion device is configured to retract and securely retain the needle in an inaccessible portion of the insertion device after insertion of the cannula or other subcutaneous element. In embodiments, the subcutaneous insertion system can further comprise a set comprising tubing and configured to be removably coupled to the site while on the skin of the patient in order to convey fluid from a source coupled to the set to the patient via the tubing, site and cannula. In still other embodiments, devices and elements other than tubing sets can be mechanically, electrically and/or communicatively coupled with the site following application to the skin of the patient. The site (or "payload") can be circular, elliptical, rectangular, or modifications of those general shapes.

While the type of surface device and subcutaneous element can vary in embodiments, examples discussed herein generally relate to an infusion site comprising a cannula. These examples are used without limitation or effect on the scope of the claims, as various other types of devices and elements are contemplated and may or may not fall within the scope of the claims. Some of these other devices and elements include patient monitoring systems and devices used to check or monitor one or more conditions of a patient (e.g., blood levels such as glucose, carbon dioxide, or oxygen) or body temperature, which also can include a device applied to the skin and comprising a cannula, filament, wire, sensor or other device introduced at least partially subcutaneously. Still other devices can be used in embodiments for application in or on the skin of a patient, including those with a different type of or without a subcutaneous element, with a plurality of subcutaneous elements, or with a subcutaneous element as well as surface elements (e.g., sensors or other devices configured to monitor a patient condition at the surface of the skin, independent of or in combination with a subcutaneous element). In some embodiments, a site may comprise a "patch pump" or similar device which may include its own fluid reservoir, power mechanism, power supply, electronic circuitry and cannula insertion system.

Referring to FIG. 1, an exploded view of an embodiment of an insertion device 100 is depicted. As depicted, insertion device 100 comprises a housing 110, a needle hub assembly 120, a cylinder hub 130, a biasing element 140, a sleeve 150, a cap 160 and a lock pin 170.

Lock pin 170 secures cap 160 to housing 110 via an aperture 172 in housing 110 and an aperture 174 in cap 160 and can also abut or otherwise interact with sleeve 150 to prevent sleeve 150 from moving within housing 110 and cap 160. This can prevent inadvertent activation of insertion device 100, such as if insertion device was inadvertently dropped or jarred, while also providing a child safety feature. Lock pin 170 can form part of or be coupled with a tear-away band 176 that can be part of cap 160 or housing 172, such that removing tear-away band 176 removes lock pin 170 and enables cap 160 to be decoupled from housing 110 while also freeing sleeve 150 for movement. Cap 160 can comprise a label 161 in embodiments, wherein the label identifies at least one of a manufacturer of insertion device 100, name of insertion device 100, a serial number of insertion device 100, a barcode or other computer-readable identifier, instructions or warnings with respect to use of insertion device 100, and the like. Cap 160 can include a raised annular rib around its inner surface near the proximal end. This rib can be continuous or discontinuous. In some embodiments, the choice of cap design could be influenced by the sterilization method used on the device.

Insertion device 100 can be preloaded with or otherwise comprise a site 180 including a central hub 181 extending upwardly from a top surface or side of site 180. In still other embodiments, site 180 is not pre-loaded within insertion device 100 and instead can be coupled with insertion device 100 just prior to application of site 180 to the skin of the patient. Site 180 can be coupled with a site pad 182 and sleeve pad 184 on a bottom surface or side opposing its top surface. In other embodiments in which site 180 is differently configured and/or comprises a different type of device, the configuration of site pad 182 and/or sleeve pad 184 can vary, or one or both could be omitted or replaced by a different element. Here and elsewhere in this document unless otherwise specified, a "top" surface generally refers to an upper surface as the drawing is oriented on the page, while a "bottom" surface generally refers to the opposite, lower surface in the drawing, without limitation with respect to how the device or element may be oriented in use and operation or other situations. This convention is used for other elements and features herein throughout as well, unless otherwise specified.

Site pad 182 can couple or interface between site 180 and sleeve pad 184, while sleeve pad 184 can be configured to removably secure site 180 to sleeve 150 before application of site 180 to the skin of a patient. Sleeve pad 184 can comprise an adhesive layer, such as one comprising TEGA-DERM or another similar adhesive suitable for application to human skin or tissue, to removably couple site 180 to the skin of a patient after activation of device 100, which separates sleeve pad 184 from sleeve 150 as site 180 is applied to the skin of the patient. The adhesive layer can be applied to or coupled with a bottom surface of sleeve pad 184, or in another embodiment the adhesive layer can be applied to or coupled with a different surface of or coupled to site 180. In FIG. 1, a top surface of sleeve pad 184 is visible. Sleeve pad 184 can also comprise a finger tab 186, which can be an additional layer of material or an area free of adhesive between sleeve pad 184 and the skin of the patient to enable the patient or a clinician to easily grasp and remove site 180 from the skin of the patient or otherwise hold site 180 via sleeve pad 184 with no or reduced interaction with the adhesive layer.

One, some or all of site 180, site pad 182 and sleeve pad 184 can be precoupled with one another within insertion device 100 (i.e., combined or assembled together during manufacturing of insertion device 100), or in some embodiments they can be separate components combined upon activation of device 100. For example, in one embodiment site 180 and site pad 182 are precoupled with one another within insertion device 100 during manufacturing, and subsequently the combination is coupled with sleeve pad 184, via an additional adhesive layer on a top surface of sleeve pad 184 and/or on a bottom surface of site pad 182, only upon activation of device 100 to apply site 180, along with site pad 182 and sleeve pad 184, to the skin of a patient. The perimeter 191 of each of site 180, site pad 182 and sleeve pad 184 can be a variety of shapes. As shown in FIGS. 1A-H, the general perimeter 191 may be round, elliptical, oblong, rectangular, semi-rectangular, rounded rectangular, square, rounded square or some other shape in various embodiments. The site 180, site pad 182 and sleeve pad 184 may have a combination of such perimeter shapes as well. In one embodiment, for example, site 180 and site pad 182 have generally round perimeters while sleeve pad 184 has a generally elliptical perimeter.

Figure 2A:
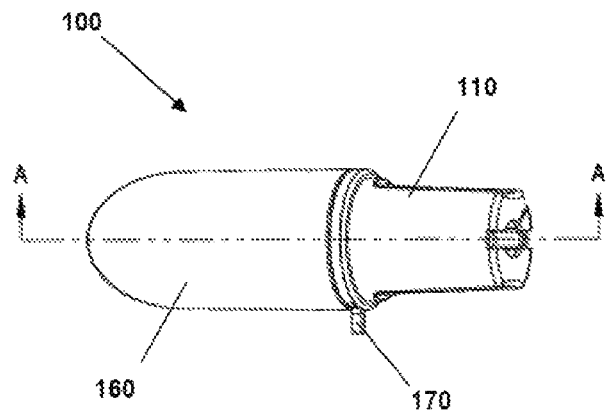
FIG. 2A is a top view of an insertion device in a "shipped" state according to an embodiment.
Figure 2B:
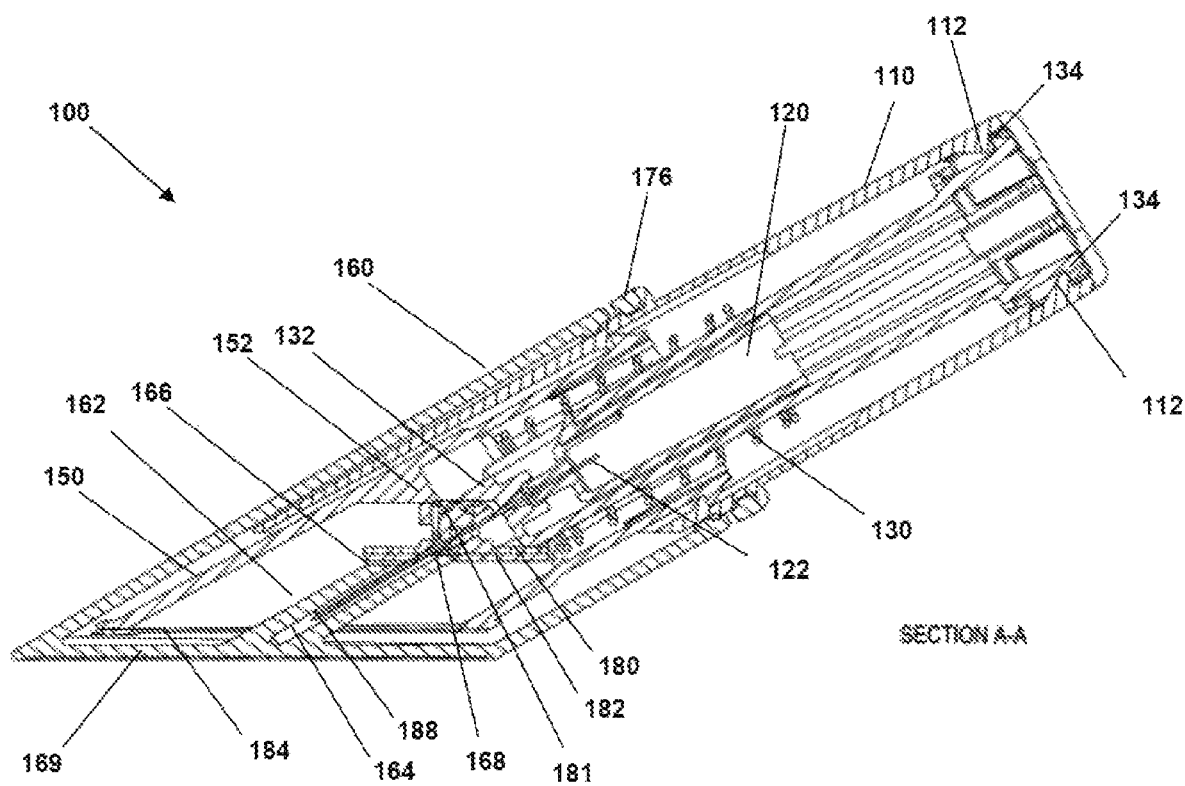
FIG. 2B is a side cross-sectional view of the insertion device of FIG. 2A.

FIG. 2A depicts a top view of insertion device 100 in which cap 160 is secured to housing 110 by lock pin 170, and FIG. 2B depicts a side sectional view of insertion device 100. A subcutaneous element, such as a cannula 188, extends from the bottom surface of site 180 at an angle greater than 0 degrees and less than 90 degrees with respect to that bottom surface. In embodiments, cannula 188 can be at an angle α (see FIG. 6E) of between about 20 degrees and about 50 degrees, such as between about 25 degrees and about 35 degrees, for example about 30 degrees. In other embodiments, cannula 188 can instead comprise a wire, filament, sensor, or other device or element configured to be inserted at least partially subcutaneously. An embodiment comprising a cannula is discussed herein by way of example only.

Site pad 182 and sleeve pad 184 each comprise an aperture 183 and 185 (see FIG. 1), respectively, that enables cannula 188 to pass through site pad 182 and sleeve pad 184 when site 180 is applied to the skin of a patient. Apertures 183 and 185 can be elliptical, which can be more easily compatible with the angle of cannula 188, or round or some other shape. Apertures 183 and 185 can have the same or different shapes, circumferences, relative placements on site pad 182 and sleeve pad 184, respectively, and other features and characteristics.

FIGS. 2A and 2B depict insertion device 100 in a post-manufacturing shipped state, and in an embodiment in which site 180 is preloaded in insertion device, and cap 160 is secured to housing 110 by lock pin 170 and includes tear-away band 176. Cap 160 comprises a cap post 162 extending upwardly or away from an inner bottom surface of cap 160 at a similar angle as cannula 188. Cap post 162 is hollow or otherwise comprises an interior channel 164 to house cannula 188 in the shipped state. The top or open end of cap post 162 is configured to support site 180. In one embodiment, the open end of cap post 162 is stepped or graduated such that a first portion 166 of cap post 162 supports site 180 near one side or edge of site 180 and a second portion 168 of cap post 162 supports site 180 at or near its center, accommodating the relative angles between site 180 and cap post 162. As such, in embodiments second portion 168 and one or both of apertures 183 and 185 are arranged to enable second portion 168 to pass therethrough and contact the bottom surface of site 180 proximate, such as adjacent to or at least partially around, cannula 180. In embodiments, one or both of first and second portions 166 and 168 can be configured to engage with a corresponding portion of site 180 to more securely support site 180 within insertion device 100.

Site 180 is also supported or held in place within insertion device 100 by an end portion 132 of cylinder hub 130 and trigger rib 152 of sleeve 150. End portion 132 and trigger rib 152 can abut and/or support at least a portion of a central hub 181 of site 180. In one embodiment, end portion 132 can further be configured to abut and/or support at least a portion of the top surface of site 180. Thus, like the end of cap post 162 having first and second portions 166 and 168, end portion 132 of cylinder hub 130 is also configured to support site 180 in an orientation in which the top and bottom surfaces of site 180 are neither parallel nor perpendicular with the sidewalls of housing 110 and cap 160. The bottom surface of site 180 is generally parallel to the top surface of sleeve pad 184. In an embodiment shown in FIG. 2, site 180 is generally parallel with an end portion 169 of cap 160, wherein end portion 169 is not perpendicular with the sidewall of cap 160 and is not parallel with an end surface of housing 110. In general, the angle between end portion 169 and the sidewall of cap 160, as well as the angle between the top and bottom surfaces of site 180 and the sidewalls of cap 160 and housing 110, is similar to the angle at which cannula 188 extends from the bottom surface of site 180 (i.e., an angle between about 20 degrees and about 50 degrees, such as between about 25 degrees and about 35 degrees, for example about 30 degrees, in various embodiments). In some embodiments, end portion 169 of cap 160 is not parallel to the bottom surface of site 180 and the angle between end portion 169 of cap 160 and the sidewalls of housing 110 and cap 160 may be a different angle, such as a right angle.

Figure 3A:
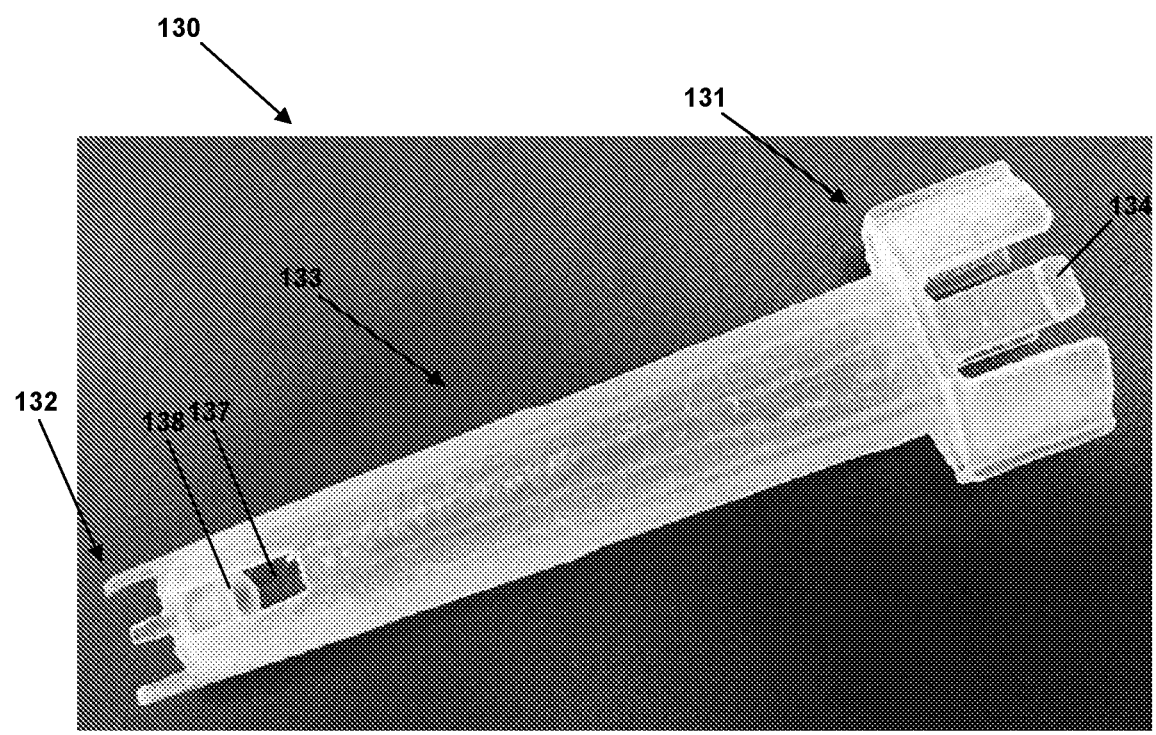
FIG. 3A is a top perspective view of a cylinder hub of an insertion device according to an embodiment.
Figure 3B:
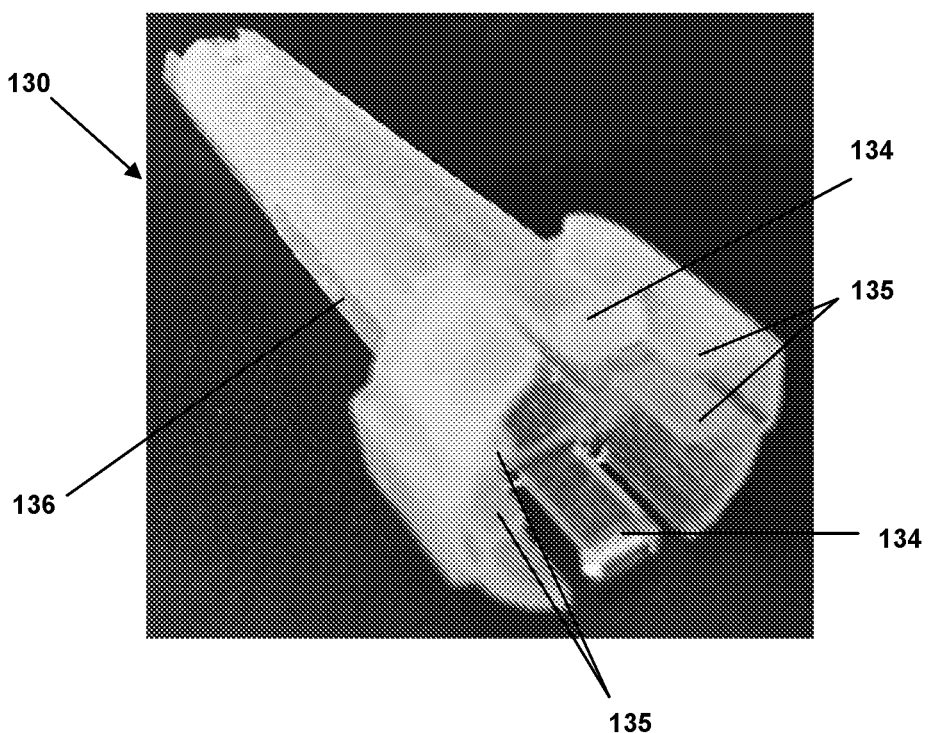
FIG. 3B is an end perspective view of the cylinder hub of FIG. 3A.
Figure 4:
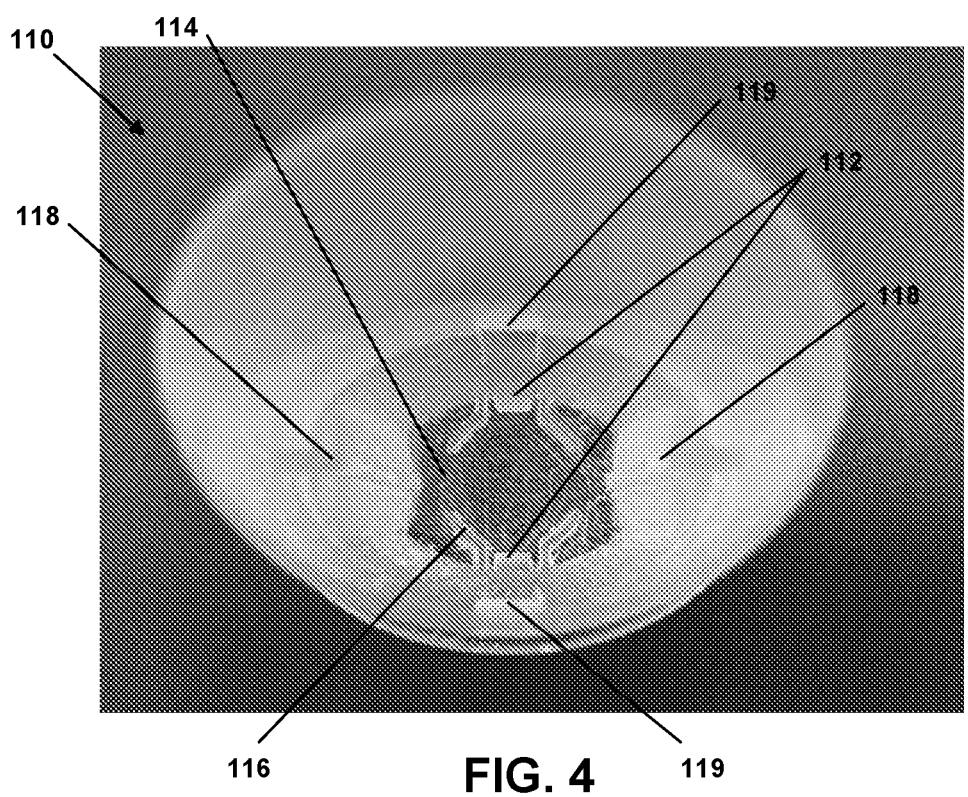
FIG. 4 is an end perspective view of a housing of an insertion device according to an embodiment.

Referring also to FIGS. 3A and 3B, cylinder hub 130 is generally hollow and comprises a shoulder portion 131 and a body portion 133. Shoulder portion 131 can have a generally ovular or oblong cross-section, while body portion 133 also can be generally ovular, oblong or round. In one embodiment, body portion 133 tapers slightly (i.e., the cross-section diameter decreases) between shoulder portion 131 and a distal end of cylinder hub 130. Shoulder portion 131 can comprise two tabs 134 configured to engage with shoulders 112 (see FIG. 2B) of housing 110 to couple cylinder hub 130 and housing 110 with at least a portion of shoulder portion 131 abutting an inner surface of an end of housing 110. In one embodiment, and referring also to FIG. 4, an internal top surface 114 of housing 110 can comprise a standing circular rib 116 configured to interface with shoulder portion 131 to hold shoulder portion in place within housing 110. Housing 110 also comprises guide ribs 118 and sleeve tabs 119.

Cylinder hub 130 further comprises apertures 136 (see FIG. 1) extending from a first end of cylinder hub 130, through shoulder portion 131 via internal guides 135 that form a channel in shoulder portion 131 to connect with apertures 136 formed in body portion 133. Apertures 136 are configured to guide needle hub 120 within cylinder hub 130 and extend from shoulder portion 131 to about a midpoint of body portion 133. Apertures 136 are formed opposite each other, on opposing sides of cylinder hub 130.

Body portion 133 comprises an aperture 137 configured to interact with a corresponding tab on needle hub 120. Body portion 133 also comprises a needle guide 138 and previously mentioned end portion 132 that abuts site 180 as discussed above.

Figure 5A:
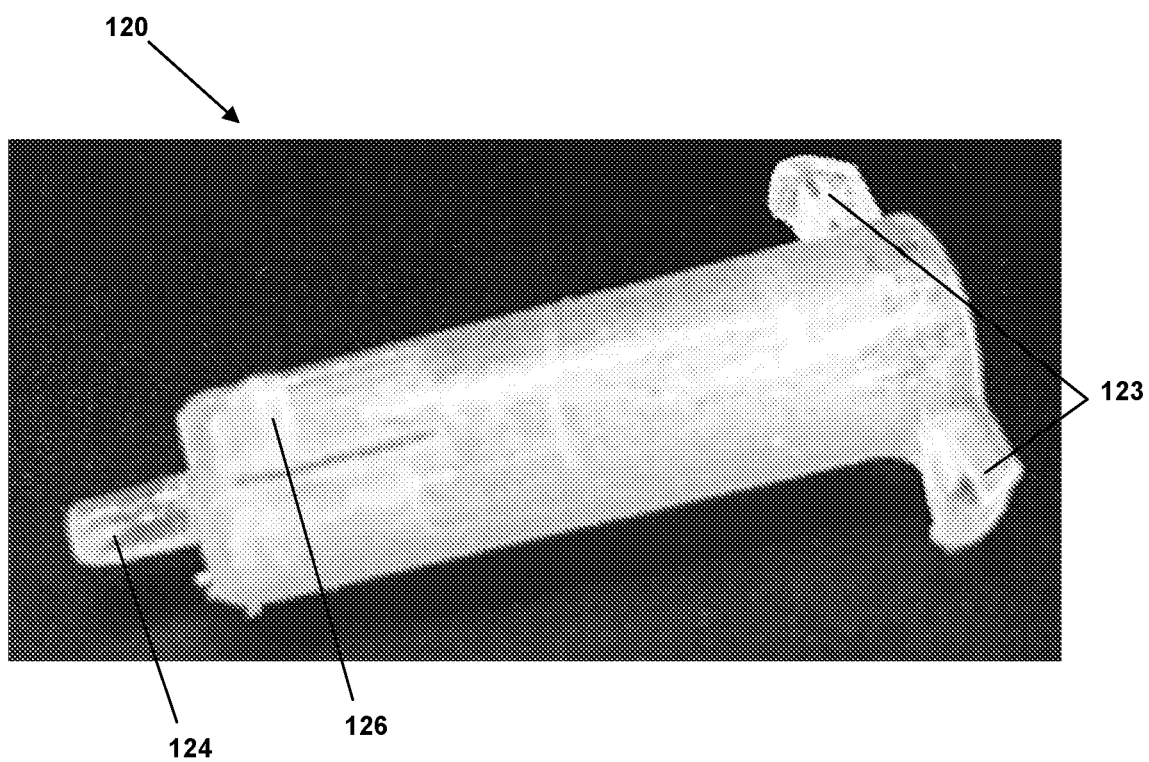
FIG. 5A is a side perspective view of a needle hub of an insertion device according to an embodiment.
Figure 5B:
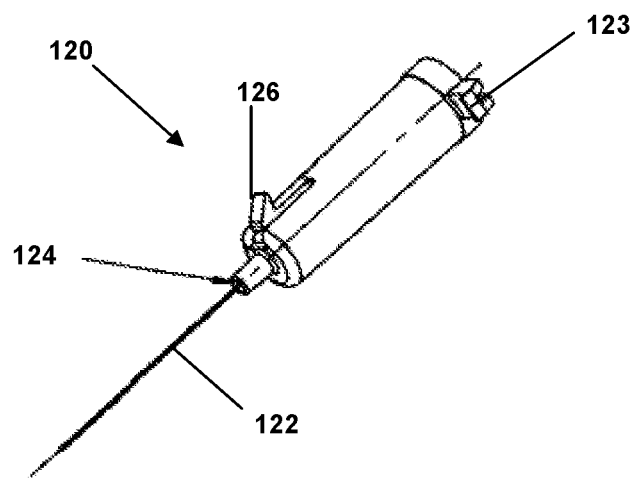
FIG. 5B is a side perspective view of a needle hub of an insertion device according to an embodiment.
Figure 5C:
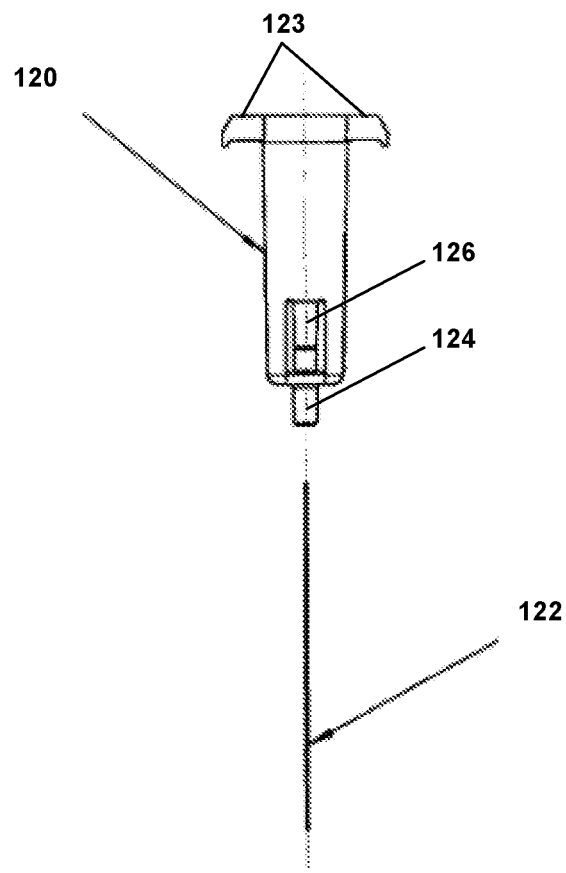
FIG. 5C is a side exploded view of a needle hub of an insertion device according to an embodiment.

Referring to FIGS. 5A, 5B and 5C, needle hub 120 is configured to be slidably arranged within the hollow cylinder hub 130 (see FIG. 3A). Needle hub 120 comprises tabs 123 configured to slide within guides 135 and apertures 136 of cylinder hub 130 (see FIG. 3B). Tabs 123 also can interact with biasing element 140 (see FIG. 1), such as to compress biasing element toward site 180 (as depicted in FIG. 2B). Needle hub 120 further comprises needle retaining portion 124 and snap arm 126. During use and operation, snap arm 126 interacts with both aperture 137 (see FIG. 3A) of cylinder hub 130 (to initially retain needle hub 120 proximate needle guide 138) and trigger rib 152 (see FIG. 2B) (to disengage snap arm 126 from aperture 137 to cause needle hub 120 and needle 122 to be retracted within housing 110.

Figure 6A:
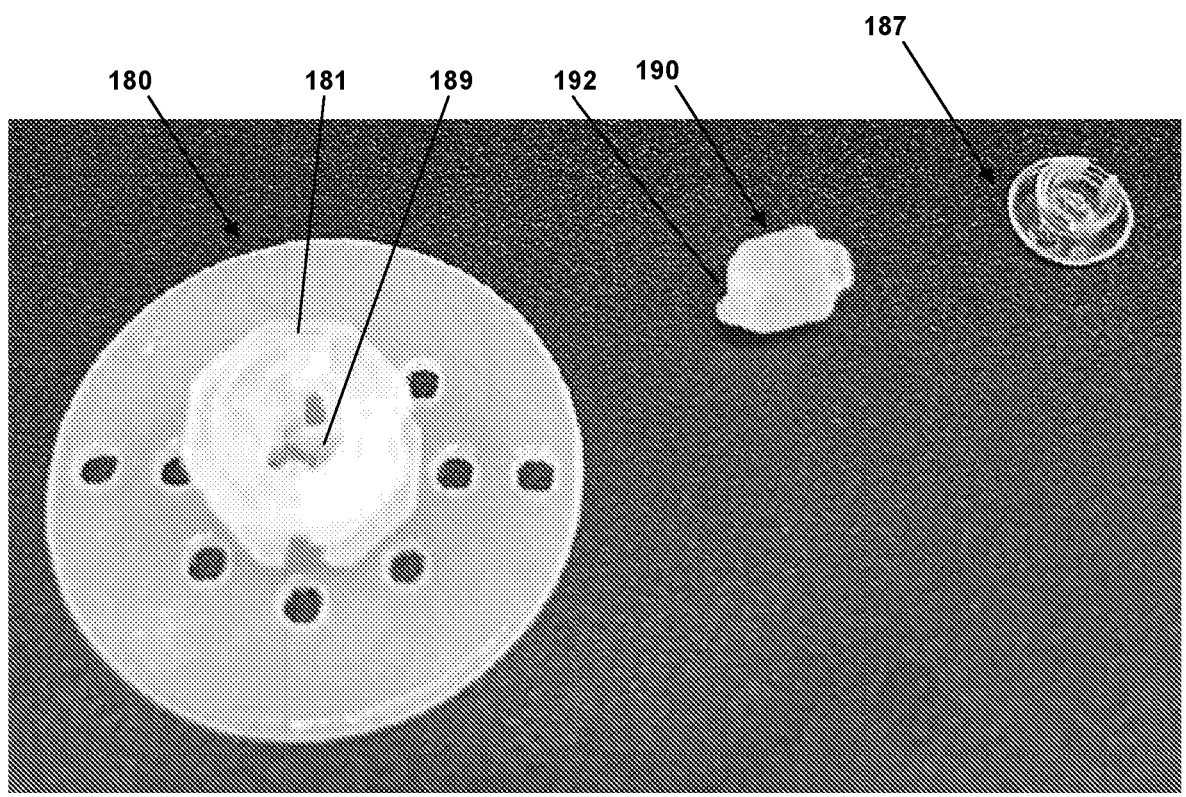
FIG. 6A is a top exploded view of a site according to an embodiment.
Figure 6B:
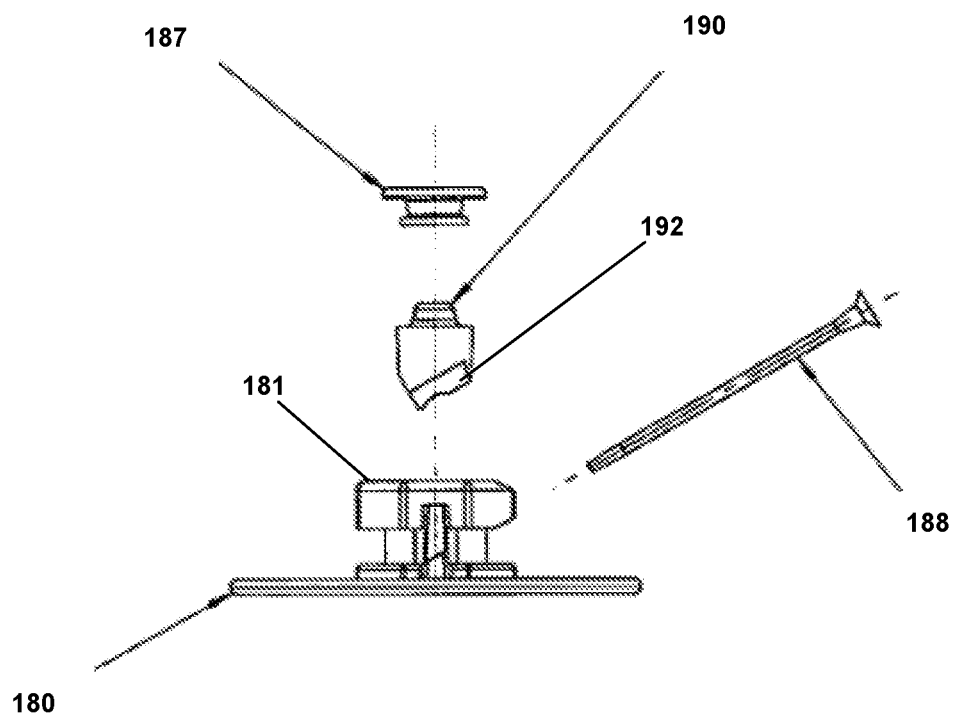
FIG. 6B is a side exploded view of a site according to an embodiment.
Figure 6C:
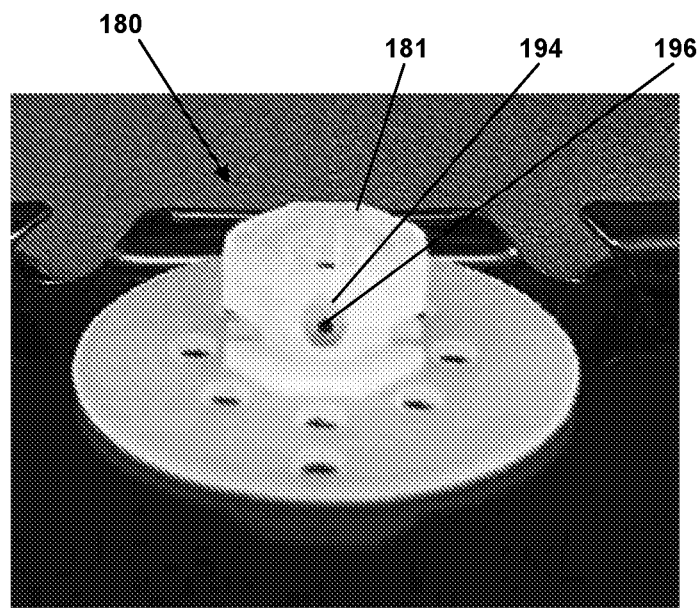
FIG. 6C is a back side view of a portion of a site according to an embodiment.
Figure 6D:
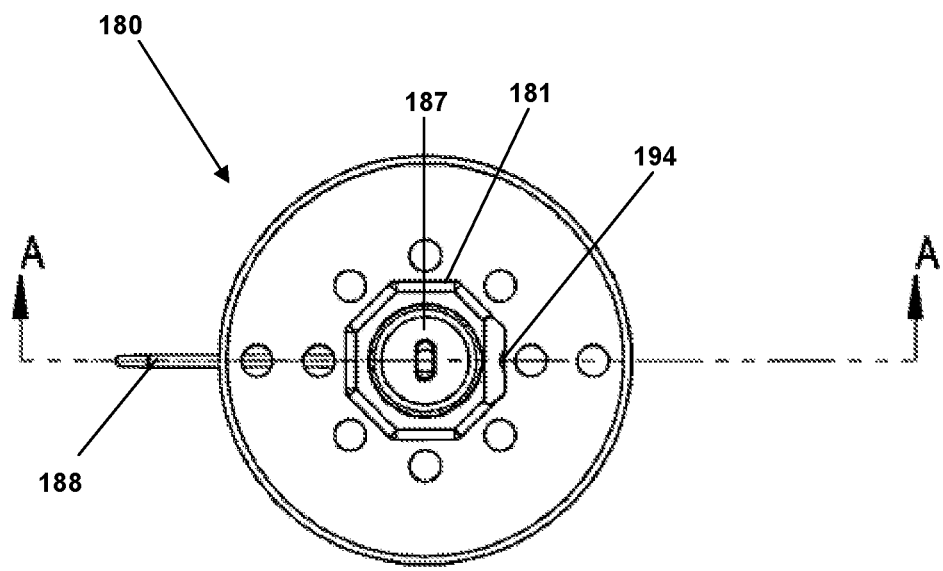
FIG. 6D is a top view of a site according to an embodiment.

Referring to FIGS. 6A, 6B, 6C, 6D and 6E, site 180 is depicted, along with septum 190 and site cap 187. Septum 190 is configured to fit within central hub 181 and facilitate fluid communication between needle 122 and cannula 188 in use. As can be seen in FIG. 6A, septum 190 is asymmetrical, having a slanted lower portion 192. An inner surface 189 of central hub 181 is correspondingly slanted to accommodate septum 190. Site cap 187 fits on central hub 181 over septum 190 to secure septum 190 therewithin. In use and operation of insertion device 100, needle 122 enters site 180 via a side aperture 194 formed in central hub 181. Needle 122 passes through septum 190 within central hub 181 and exits site 180 via needle aperture 196. As needle 122 passes through needle aperture 196, needle 122 enters cannula 188 (not shown in FIGS. 6A and 6C) to insert cannula into the skin of a patient as site 180 is applied to the skin of the patient. Needle 122 is then removed and retracted within insertion device 100, as will be discussed more below.

Referring to FIGS. 6F, 6G, 6H, 6I, 6J, and 6K, a septum 190 is depicted from various perspectives, for use in a site 180. Specifically, the views shown are side, bottom, back side, front side, and multiple perspective views, respectively. As shown, septum 190 is generally made up of a main body portion 193, an upper protrusion 195, and a slanted lower portion 192. Main body portion 193 is generally a vertically disposed, cylindrical member which surrounds a cylindrical cavity 197. Extending vertically from main body portion 193 is a tapered, generally conical, upper protrusion 195. Further, the main body portion 193 is merged with a smaller diameter, generally cylindrical, slanted lower portion 192 that extends across the bottom of the main body portion 193 in an angled manner. Lower portion 192 has a planar, angled face 198 at its lower end. This angled face 198 contains an arch shaped aperture 199 that provides a channel 177 that extends partially through the slanted lower portion 192 and merges with the cylindrical cavity 197 of the main body portion. Further, the slanted lower portion 192 further contains a lower aperture 178 that provides access to the cylindrical cavity 197 from the bottom of the septum 190. This lower aperture 178 further provides a small recess from the bottom surface of the lower portion 192.

Accordingly, the channel 177 formed within the septum 190 provides angled access for a cannula 188 that is inserted through a site 180 at various angles. The contours of the arch shaped aperture 199 and channel 177 provide a versatile and functional passage and arrangement for cannula insertion. Accordingly, the when the cannula 188 is inserted through the aperture 196, wall 179, and channel 177 of lower portion 192, a convenient seal is made possible by the septum 190.

Figure 7:
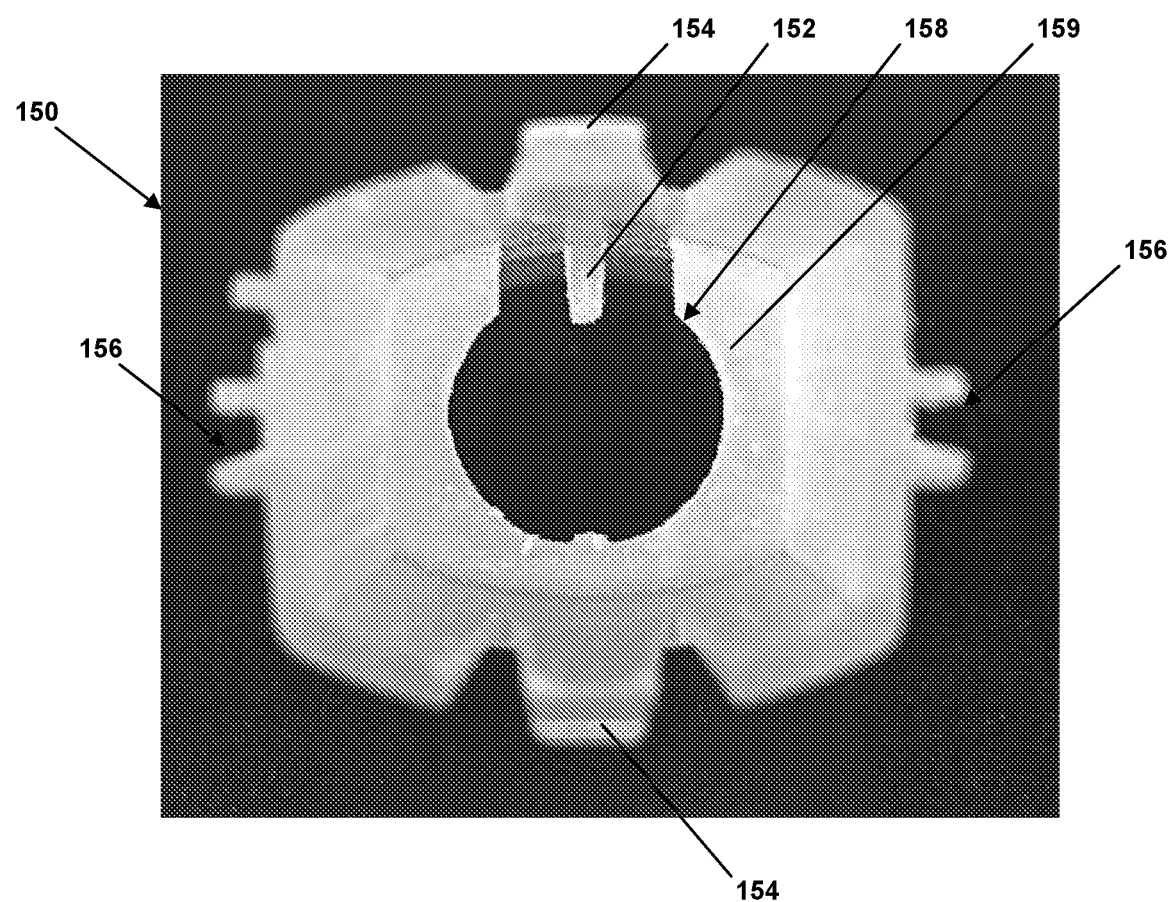
FIG. 7 is an end perspective view of a sleeve of an insertion device according to an embodiment.

Sleeve 150 is depicted in FIG. 7. Sleeve 150 comprises trigger rib 152. Sleeve 150 further comprises tabs 154 and guide channels 156, each of which interacts with a corresponding portion of housing 110: tabs 154 can interlock with sleeve tabs 119 (see FIG. 4) while guide channels 156 can guide sleeve ribs 118 (see FIG. 4) on each side. The ends of guide channels 156 can prevent further relative movement of housing 110 and sleeve during operation. Cylinder hub 130 is configured to be arranged through central aperture 158, while a rib 159 in which central aperture 158 is formed can be a stop or fixing point for biasing element 140, such that biasing element 140 is arranged between tabs 123 of needle hub 120 and rib 159 in at least one operational state of insertion device 100.

Biasing element 140 can comprise a spring, such as a coil spring, in embodiment. In other embodiments, some other type or form of biasing element can be used. As discussed below, biasing element 140 is compressed during application of site 180, and release of the compression retracts needle 122 during use and operation of insertion device 100.

Figure 8A:
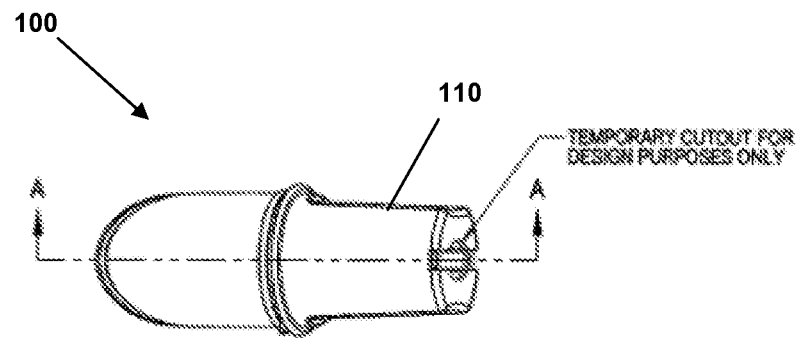
FIG. 8A is a top view of an insertion device in a "triggered" state according to an embodiment.
Figure 8B:
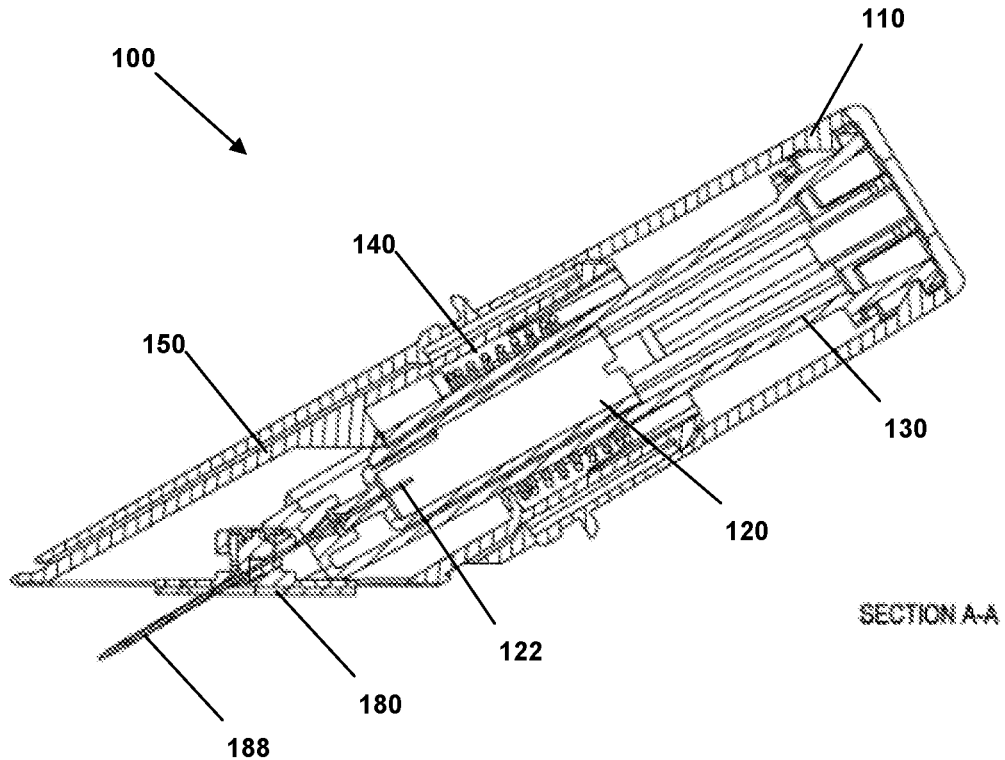
FIG. 8B is a side cross-sectional view of the insertion device of FIG. 8A.

Referring to FIGS. 8A and 8B, insertion device 100 is depicted in a "triggered" state. To achieve the "triggered" state from the "shipped" state depicted in FIG. 2A, lock pin 170, tear-away band 176 and cap 160 are removed. Insertion device 100 is placed on the skin of the patient, with the open bottom portion of sleeve 150 against and substantially parallel with the skin of the patient. Housing 110 is pushed toward the skin of the patient while sleeve 150 remains generally stationary with respect to the skin of the patient. This advancement of housing 110 causes site 180 and cannula 188, cylinder hub 130, needle hub 120 and needle 122 to advance toward the skin of the patient until site pad 182 is in contact with sleeve pad 184 that is already in contact with the skin of the patient and needle 120 has inserted cannula 188 into the skin of the patient. At the same time, biasing element 140 is compressed. This is generally the state depicted in FIG. 8B, although sleeve pad 184 is not specifically depicted in this view.

In FIG. 8B, cannula 188 would be inserted into the skin of a patient if so applied, and cannula 188 would enter the skin of the patient at an angle between 0 degrees and 90 degrees, as discussed above. In embodiments, cannula 188 is about 6 mm to about 25 mm long, such as about 13 mm long in one example embodiment and such as about 19 mm in another example embodiment. The length of cannula 188 can vary in other embodiments. Another advantage of the angled insertion of cannula 188 can be an increased resistance to potential escape of the medicament being infused, which might occur if a portion of the medicament were to follow the exterior surface of cannula 188 to the surface of the patient's skin. More particularly, if cannula 188 is inserted at an angle between 0 degrees and 90 degrees, such as about 30 degrees, instead of at 90 degrees as is conventional, cannula 188 can be longer, such as twice as long or more, yet penetrate to the same depth within the subcutaneous layer of the patient's skin.

Once housing 110, cylinder hub 130 and needle hub 120 advance sufficiently toward the patient's skin so that snap arm 126 (see FIG. 5B) of needle hub 120 reaches trigger rib 152 (see FIG. 7), trigger rib 152 causes snap arm 126 to disengage from aperture 137 (see FIG. 3A). Because biasing element 140 has been compressed during the movement of housing 110 and cylinder hub 130 toward the skin and relative to sleeve 150, disengagement of snap arm 126 from aperture 137 by trigger rib 152 causes needle hub 120 and needle 122 to be retracted upwardly away from the skin within cylinder hub 130 and housing 110 by the released force of compressed biasing element 140, which engages with tabs 123 to retract needle hub 120. Insertion device is then in a "retracted" state.

Figure 9A:
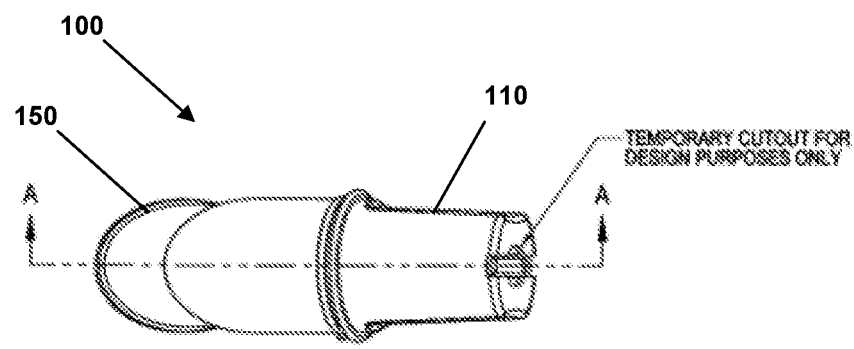
FIG. 9A is a top view of an insertion device in a "retracted" state according to an embodiment.
Figure 9B:
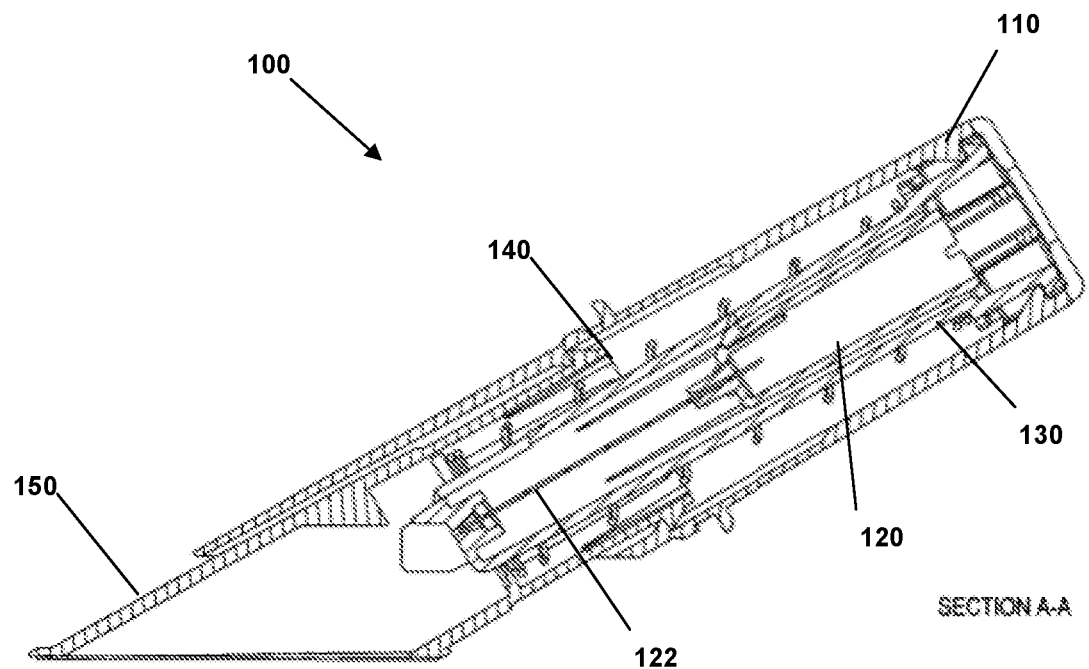
FIG. 9B is a side cross-sectional view of the insertion device of FIG. 9A.

Referring to FIGS. 9A and 9B, the "retracted" state of insertion device 100 is depicted. Needle hub 120 is retracted within cylinder hub 130 and housing 110 until needle 122 is substantially or fully within cylinder hub 130, such that it cannot be accessed or inadvertently "stick" someone after it has now been used to apply site 180 and insert cannula 188. Biasing element 140 is generally relaxed, or at least less compressed than in either the "shipped" or "triggered" states.

Once site 180 has been applied to the skin of a patient, an infusion set can be coupled to site 180 to enable an infusion pump or other fluid source to deliver a fluid to the patient via site 180, in an embodiment in which site 180 is used for infusion. Examples of infusion sets are disclosed in U.S. Pat. No. 9,192,717 to Cote et al., which is incorporated herein by reference in its entirety. In embodiments, the set can be coupled to site 180 in a plurality of different relative positions (i.e., to change the side or angle from which infusion tubing of the set extends from site 180 to increase comfort and convenience to the patient). In one embodiment, an infusion set can be coupled to site 180 in at least different relative positions, such as with the needle of the set entering site 180 from one of four different sides spaced apart from another by about 90 degrees. In other embodiments, more or fewer relative coupling relationships between site 180 and the set are possible. Upon being coupled to site 180, a needle within the set passes through a side of central hub 180 and pierces septum 190, establishing fluid communication between the needle (and medical tubing coupled thereto via the rest of the set, such as from an infusion pump) and cannula 188.

In still other embodiments, devices other than infusion sets and tubing can be coupled to site 180. In embodiments, this coupling can be mechanical, electrical, communicative or some combination of these coupling modalities. A set or other type of mechanical coupler can be used in embodiments, or a set can be omitted. To accommodate a variety of different coupling types and configurations, the configuration of site 180 can vary in embodiments, as can the configuration, size and orientation of some or all of the components of insertion device 100. For example, in embodiments the configuration of portions of sleeve 150, cylinder hub 130 and/or needle hub 120, which can interact with site 180 to abut and/or support site 180 within insertion device 100, can vary from those depicted as the configuration or type of payload (e.g., site 180) of insertion device 100 varies. In various embodiments, however, insertion device 100 can be used to apply, including subcutaneously, at least a portion of a site or other device at an angle between 0 degrees and 90 degrees to the skin of a patient. In some embodiments, the insertion needle passageway through the site can always be used for attachment of a set buckle to the site after placement onto the skin of a patient.

Additionally, site 180 can comprise additional elements or devices that communicate, cooperate or support the subcutaneous element or that otherwise provide a desired function. For example, in embodiments site 180 can comprise a radio-frequency identification (RFID) tag, chip, circuit, memory, sensor, light-emitting diode (LED), user interface, or other device or feature. These various devices and features can collect data, such as via the subcutaneous element or independently, and provide information to a user, clinician, other caregiver, computer or system. In still other embodiments, one or more components of site 180 can communicate with an external device, such as a meter, smartphone, smart watch, tablet, handheld or bodyworn computer or device, laptop, network, computer terminal, data reader or virtually any other device. The communications can be wired or wireless and can utilize one or more communication techniques including WIFI, BLUETOOTH, near- or far-field communications, or other techniques.

Figure 6E:
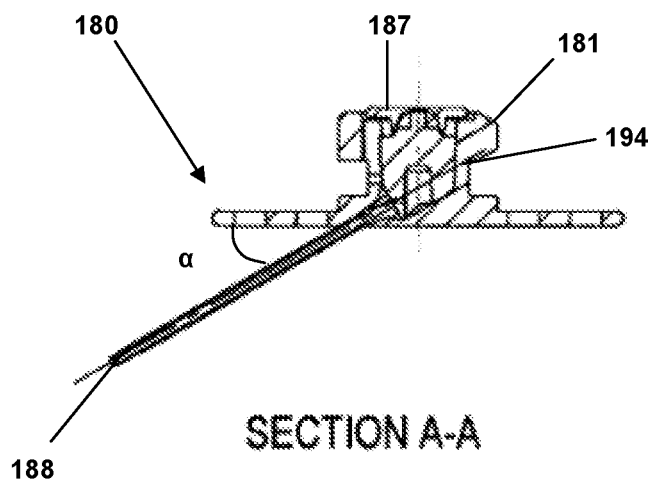
FIG. 6E is a side cross-sectional view of the site of FIG. 6D.
Figure 6F:
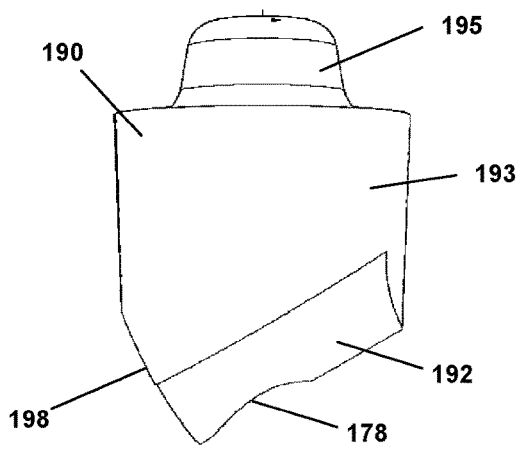
FIG. 6F is a side view of a septum of a site accordingly to an embodiment.
Figure 6G:
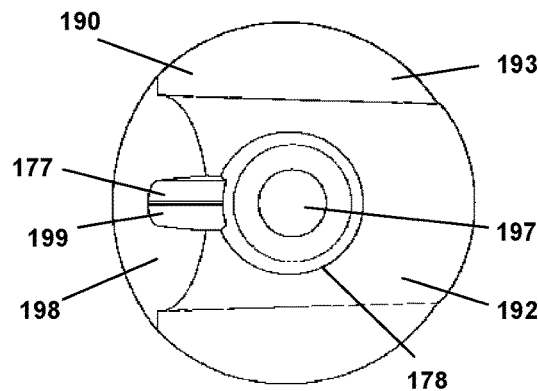
FIG. 6G is a bottom view of a septum of a site accordingly to an embodiment.
Figure 6H:
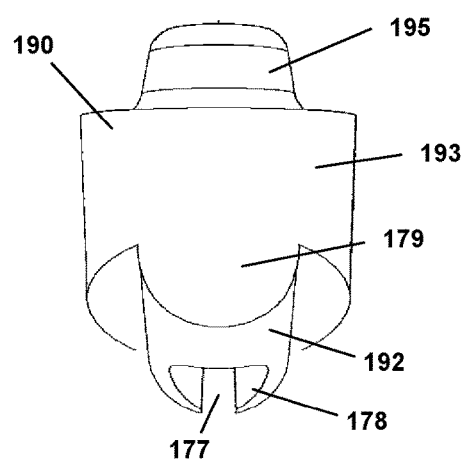
FIG. 6H is a back side view of a septum of a site accordingly to an embodiment.
Figure 6I:
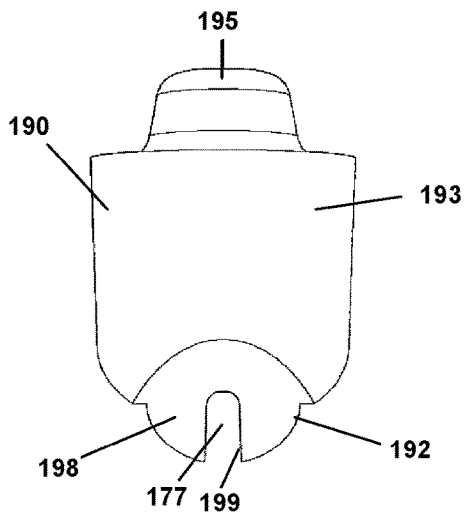
FIG. 6I is a front side view of a septum of a site accordingly to an embodiment.
Figure 6J:
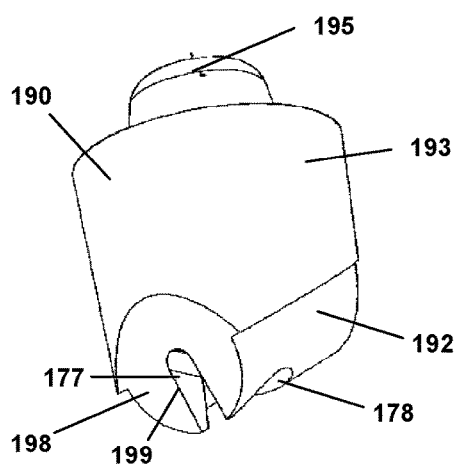
FIG. 6J is a perspective view of a septum of a site accordingly to an embodiment.
Figure 6K:
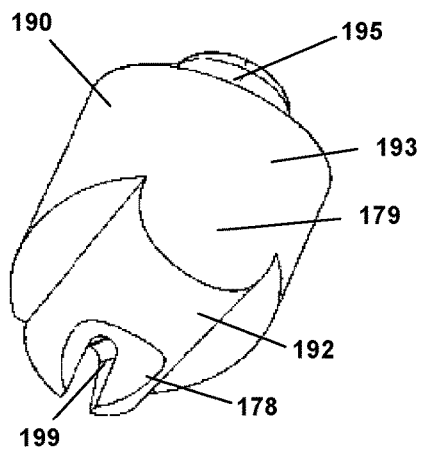
FIG. 6K is a perspective view of a septum of a site accordingly to an embodiment.
Figure 10:
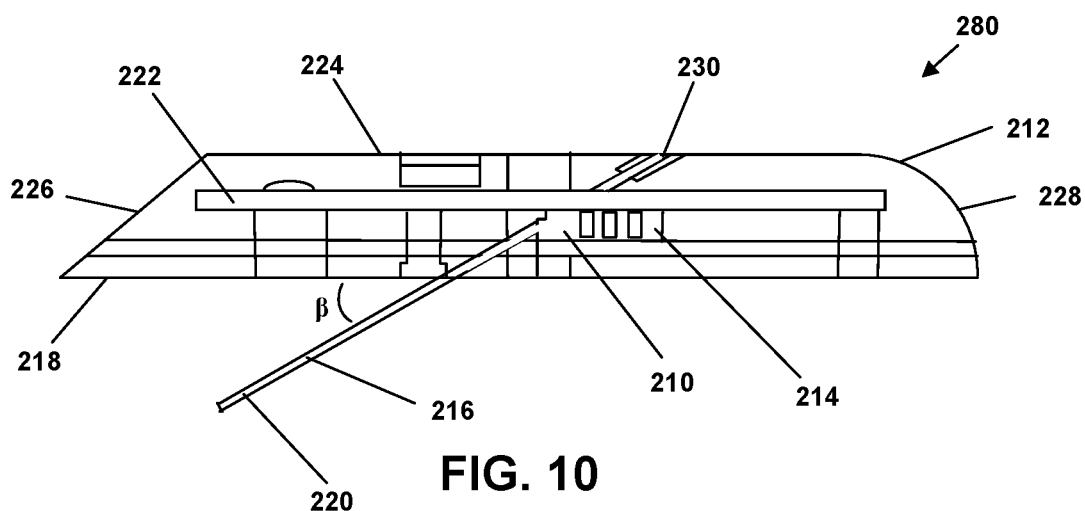
FIG. 10 is a cross-sectional side view of a site providing a sensor with a multi-surfaced housing according to an embodiment.

FIG. 10 provides a cross-sectional side view of one embodiment of a site 280 depicted in a similar orientation to site 180 shown in FIG. 6E. Site 280 provides a sensor 210, such as an analyte sensor, in a multi-surfaced, generally disc-shaped housing 212. The sensor 210 is shown with a proximal portion 214 as well as a sensing filament 216 extending from the generally flat bottom surface 218 of the housing 212 to distal portion 220 at an angle β. In some embodiments, angle β will be about 30 degrees. The angled, sensing filament 216 has advantages over a perpendicular filament as it can be twice as long and contact much more tissue in certain embodiments. In addition to one or more sensors 210, housing 212 may include a printed circuit board 222 and associated electronics. In certain embodiments, sensors 210 of this type may be used for monitoring analytes, such as glucose, in bodily fluids (blood, interstitial fluid, or others) where the sensing filament is positioned below the skin surface and monitoring is in vivo.

Housing 212 is shown with a generally planar top housing surface 224 and an angled side housing surface 226 along at least one side. The remaining side surface(s) 228 may be perpendicular to the top housing surface 224 or may gradually slope down to the bottom surface 218, as depicted in FIG. 10. The angled side surface 226 of the housing, makes it possible to appropriately fit the site 280 within the confines of an angled insertion device 100 (or 300) having a housing 110 and sleeve 150 disposed similar to the arrangement depicted in FIG. 2B. In some embodiments the angled side surface is oriented at an angle generally consistent with the sensing filament 216 or other subcutaneous element. Further, the partially angled housing surface configuration can permit mounting and delivery of site components which have a desired cross section, such as a circular cross-section. This cross-section can match a desired cross section of a sleeve 150 of an insertion device 100, for example. Top housing surface 224 contains a clearance aperture 230. This aperture 230 provides an angled hole for passage of an introducer needle 122. The housing and sensor arrangement of the site 280 accordingly permit a sensor that may be introduced and secured by angled introduction of a needle 122 and sensing filament 216.

Another type of site that may be provided by an insertion device is a "patch pump". For purposes of this application, "patch pumps" refer to small infusion pumps that can be adhered directly to the skin for wear. Such patch pumps can be used to infuse a variety of fluids or medicaments. Patch pumps include insulin pumps which can provide insulin to diabetic users; however, their usefulness can extend beyond insulin delivery to the delivery of other medicaments. In some embodiments, patch pumps involve no tubing, readily adhere to the body, are small, lightweight, completely or partially disposable, and are capable of being worn and manipulated discreetly under clothing. Some patch pumps are controlled wirelessly by a separate controller.

FIGS. 11A-17 and the corresponding description generally depict patch pumps (i.e. sites 380) and corresponding features of an insertion device 300. This insertion device 300 should be understood to generally operate in a corresponding manner to insertion device 100 with some variations necessary for the accommodation of the particular dimensions and parameters of the site 380 rather than a site 180. These differences include a different retention arrangement of the site 380 that is discussed in further detail in connection with FIGS. 13-17. While the details of a patch pump site 380 are more specifically addressed below, a sensor site 280 of similar housing shapes and/or arrangements should be understood to be fully disclosed by this description as well.

Figure 11A:
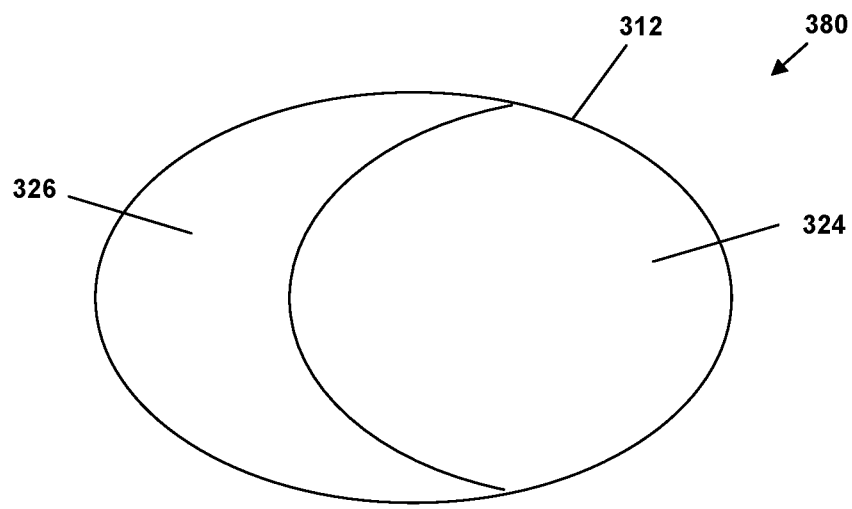
FIG. 11A is a top view of a site providing an elliptical patch pump or sensor with a multi-surfaced housing according to an embodiment.

FIG. 11A is a top view of a site or elliptical patch with a multi-surfaced housing 312 according to an embodiment. The elliptical patch pump 380 includes a generally planar top housing surface 324 and an angled side housing surface 326. The patch pump 380 is shaped and sized such that it can be applied by an angled insertion device 300 with a circular cross section across its sleeve 150. Patch pumps 380 of a variety of shapes and sizes are possible, but must be appropriately shaped to fit within the cross section of the desired angled insertion device 300.

Figure 11B:
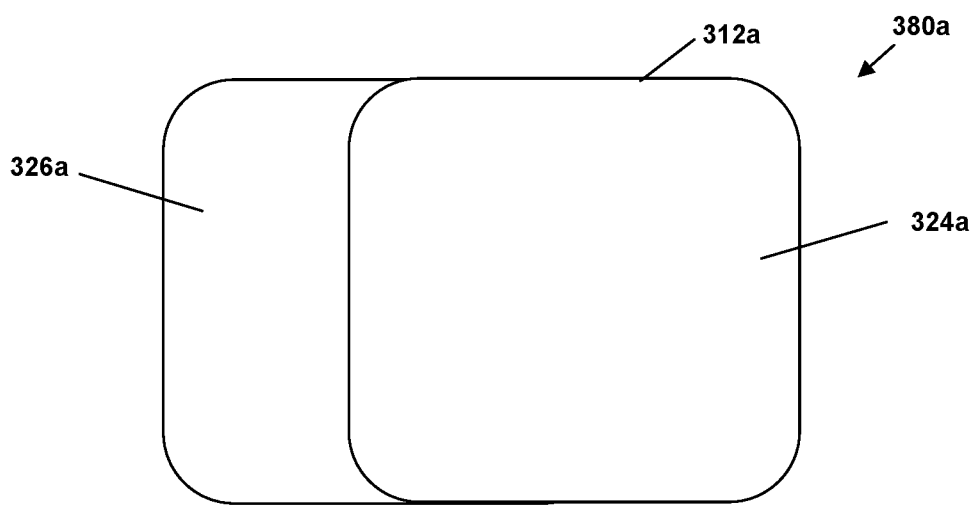
FIG. 11B is a top view of a site providing a rectangular patch pump or sensor with a multi-surfaced housing according to an embodiment.

FIG. 11B is a top view of a site constituting a rectangular patch pump 380*a* with a multi-surfaced housing 312*a* according to an embodiment. The rectangular patch pump 380*a* includes a generally planar top housing surface 324*a* and an angled side housing surface 326*a*. The patch pump 380*a* is shaped and sized such that it can be applied by an angled insertion device 100 with a square cross section across its sleeve 150.

Although not depicted in FIGS. 11A and 11B, a patch pump 380 can generally contain an adhesive pad across its bottom surface when deployed on a user in certain embodiments, which will extend beyond and around the perimeter of the housing 312. Adhesive pads of this type can be adapted for use over periods of long term wear in some embodiments.

Figure 12:
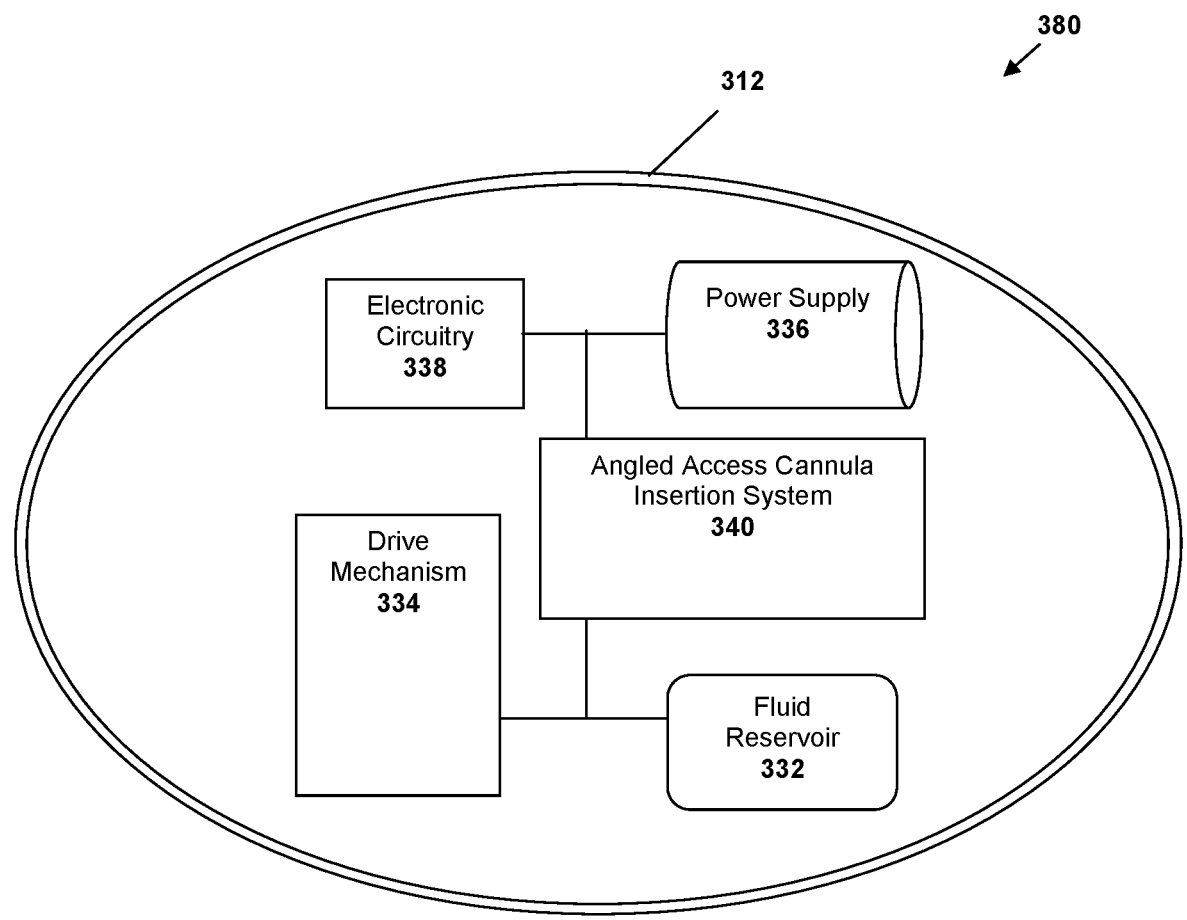
FIG. 12 is a schematic view of internal patch pump components according to an embodiment.

FIG. 12 sets forth a schematic diagram of the internal components of a patch pump 380 inside housing 312. The housing 312 can be watertight or otherwise impermeably sealed in various embodiments. The patch pump 380 generally contains a fluid reservoir 332, a drive mechanism 334, a power supply 336, electronic circuitry 338 and an angled access cannula insertion system 340. The components are generally coupled with one another, but do not require tubes or similar components subject to occlusion or similar malfunction in certain embodiments. In general, fluid reservoir 332 can hold a limited supply of insulin or other medicament. In certain embodiments, the fluid reservoir 332 may be replaceable. However, the fluid reservoir 332, or entire patch pump 380, may be disposable once the fluid reservoir 332 is used. Drive mechanism 334 can comprise a variety of types of pumping mechanisms sized for the patch pump and will generally be controlled by electric circuitry 338. The electronic circuitry 338 can program fluid delivery and communications. Electronic circuitry 338 can include a controller or can be controlled wirelessly by a controller located outside the pump housing 312. The power supply 336 can comprise one or more batteries in various embodiments. The angled access cannula insertion system 340 provides an access passageway and features which enable safe application of the patch pump 380 to a user. This cannula insertion system 340 can include all insertion related features and passages of the patch pump 380 and can be better understood in the subsequent figures and discussion of the application.

Figure 13:
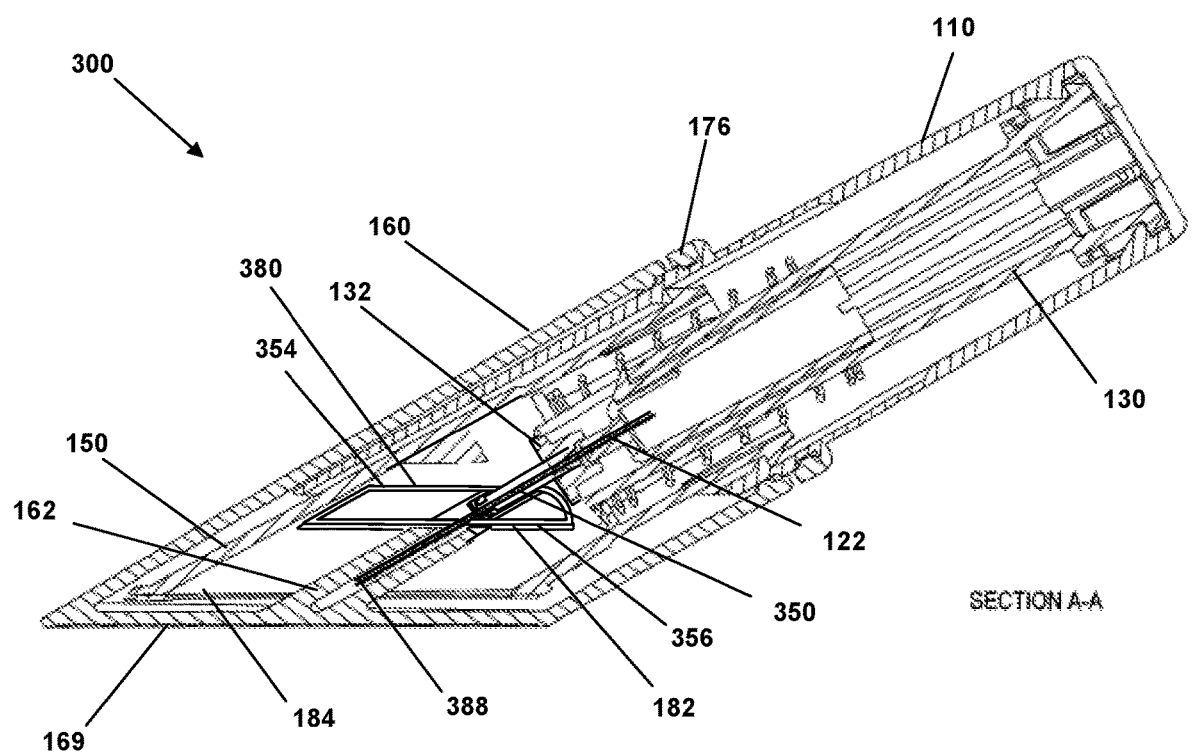
FIG. 13 is a side cross-sectional view of an insertion device in a "shipped" state using a patch pump, presented as an alternate cross-sectional view of FIG. 2A, according to an embodiment.

Referring to FIG. 13, a side cross-sectional view of an insertion device 300 in a post-manufacturing "shipped" state, for use applying a preloaded patch pump 380. This view is presented as an alternate cross-sectional view of FIG. 2A. A subcutaneous element, such as a cannula 388, extends from the bottom surface of patch pump 380 at an angle greater than 0 degrees and less than 90 degrees with respect to that bottom surface. In embodiments, cannula 388 can be at an angle β (see FIG. 16A) of between about 20 degrees and about 50 degrees, such as between about 25 degrees and about 35 degrees, for example about 30 degrees.

Site pad 182 and sleeve pad 184 each comprise an aperture that enables cannula 388 to pass through site pad 182 and sleeve pad 184 when patch pump 380 is applied to the skin of a patient. Patch pump 380 is preloaded in insertion device 300, and cap 160 is secured to housing 110 by lock pin 170 and includes tear-away band 176. In some embodiments, as shown in FIG. 13, the top or open end of cap post 162 is configured to support patch pump 380 with stepped or graduated features. In some embodiments, no cap post 162 will be present for support of a patch pump 380. In both embodiments, with or without a cap post 162, support for the patch pump 380 can also rely on an arrangement of retention fingers 350 that can extended from the end portion 132 of cylinder hub 130 into the attachment aperture 352 of the patch pump 380.

End portion 132 of cylinder hub 130 is also configured to support patch pump 380 in an orientation in which the top surface 354 and bottom surface 356 of patch pump 380 are neither parallel nor perpendicular with the sidewalls of housing 110 and cap 160. In an embodiment shown in FIG. 13, the bottom surface 356 of patch pump 380 is generally parallel with an end portion 169 of cap 160, wherein end portion 169 is not perpendicular with the sidewall of cap 160 and is not parallel with an end surface of housing 110. In general, the angle between end portion 169 and the sidewall of cap 160, as well as the angle between the top and bottom surfaces of patch pump 380 and the sidewalls of cap 160 and housing 110, is similar to the angle at which cannula 388 extends from the bottom surface of patch pump 380 (i.e., an angle between about 20 degrees and about 50 degrees, such as between about 25 degrees and about 35 degrees, for example about 30 degrees, in various embodiments). In some embodiments, end portion 169 of cap 160 is not parallel to the bottom surface of patch pump 380 and the angle between end portion 169 of cap and the sidewalls of housing 119 and cap 160 may be a different angle, such as a right angle.

Figure 14:
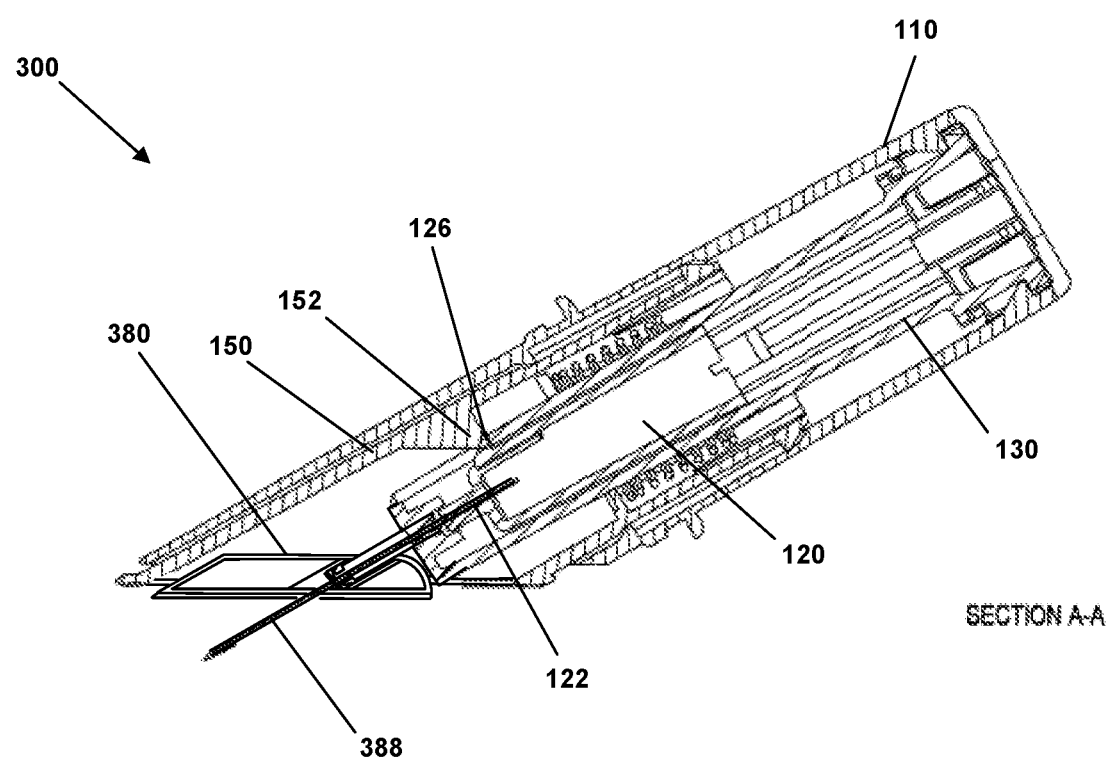
FIG. 14 is a side cross-sectional view of an insertion device in a "triggered" state using a patch pump, presented as an alternate cross-sectional view of FIG. 8A, according to an embodiment.

FIG. 14 is a side cross-sectional view of an insertion device depicted in a "triggered" state for applying a patch pump 380. This is presented as an alternate cross-sectional view of FIG. 8A. In this state, as shown, lock pin 170, tear-away band 176 and cap 160 have been removed and insertion device 300 has been placed on the skin of the patient. Specifically, the open bottom portion of sleeve 150 has been placed against and parallel with the skin of the patient. Housing 110 has been pushed toward the skin while sleeve 150 remains generally stationary with respect to the skin. Patch pump 380, cannula 388, cylinder hub 130, needle hub 120 and needle 122 have been advanced toward the skin until patch pump 380 is in contact with the skin and needle 120 has inserted cannula 388 into the skin. This arrangement would insert a cannula 388 into the skin of the patient at an angle between 0 degrees and 90 degrees.

Once housing 110, cylinder hub 130 and needle hub 120 advance sufficiently toward the skin that snap arm 126 of needle hub 120 reaches trigger rib 152, trigger rib 152 causes snap arm 126 to disengage from aperture 137. Because biasing element 140 has been compressed during the movement of housing 110 and cylinder hub 130 toward the skin and relative to sleeve 150, disengagement of snap arm 126 from aperture 137 by trigger rib 152 causes needle hub 120 and needle 122 to be retracted upwardly away from the skin within cylinder hub 130 and housing 110 by the released force of compressed biasing element 140, which engages with tabs 123 (See FIG. 5A) to retract needle hub 120. Insertion device 300 is then in a "retracted" state.

Figure 15:
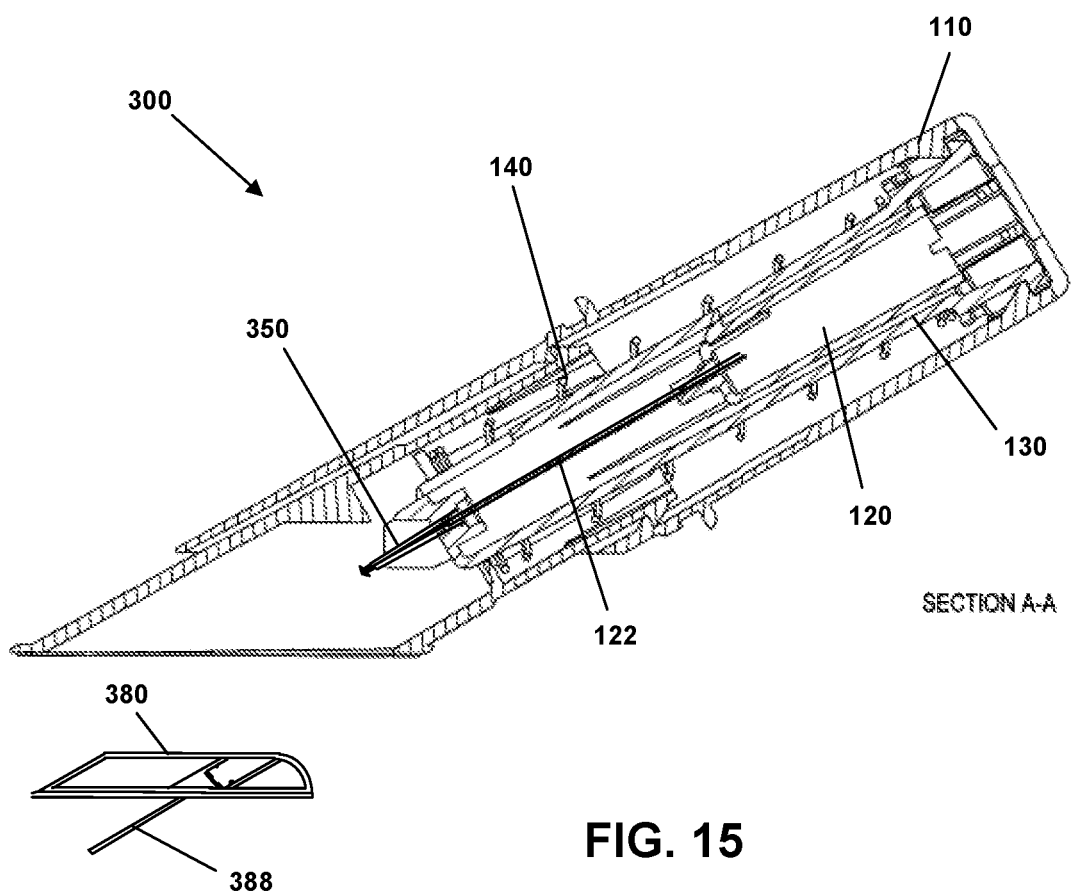
FIG. 15 is a side cross-sectional view of an insertion device in a "retracted" state using a patch pump, presented as an alternate cross-sectional view of FIG. 9A, according to an embodiment.

FIG. 15 is a side cross-sectional view of an insertion device 300 in a "retracted" state using a patch pump 380. This view is presented as an alternate cross-sectional view of FIG. 9A. Needle hub 120 is retracted within cylinder hub 130 and housing 110 until needle 122 is substantially or fully within cylinder hub 130, such that it cannot be accessed or inadvertently "stick" someone after it has now been used to apply patch pump 380 and insert cannula 388. Biasing element 140 is generally relaxed, or at least less compressed than in either the "shipped" or "triggered" states.

Once patch pump 380 has been applied to the skin of a patient, the needle 122 is retracted, leaving the cannula 388 of the patch pump 380 inserted in the desired patient location. As the needle 122 is retracted from the passageway in the pump, retention fingers 350 of the cylinder hub 130 are permitted to disengage from the patch pump 380. This disengagement results in the patch pump 380 being separated from the rest of the insertion device 300. Accordingly, retraction of the needle allows the retention fingers 350 to move inward during removal. Operation of the retention fingers 350 is described in greater detail in FIGS. 16A-17 and the related disclosure.

Figure 16A:
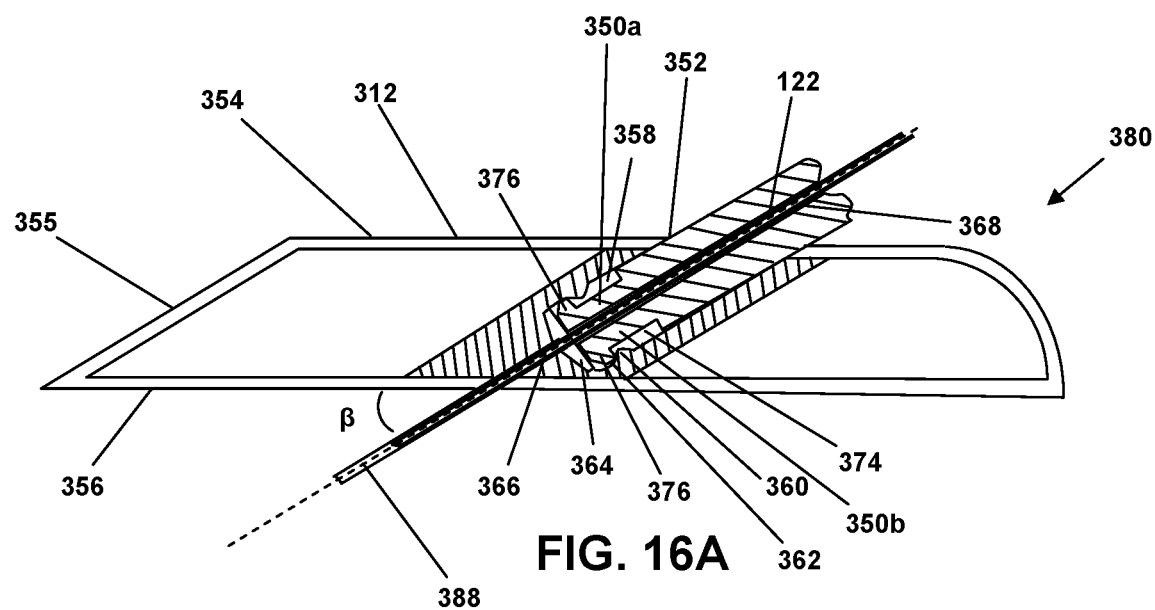
FIGS. 16A and 16B are side cross-sectional views of a patch pump retention arrangement with the cylinder hub prior to and during needle retraction, respectfully, according to an embodiment.
Figure 16B:
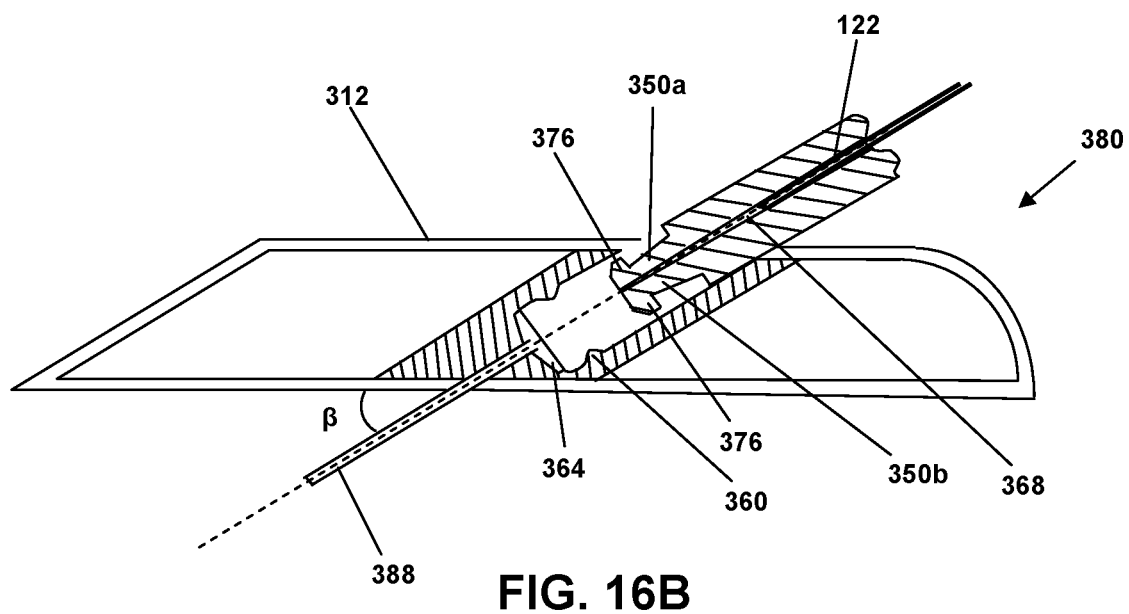

FIGS. 16A and 16B are side cross-sectional views of a patch pump retention arrangement with the cylinder hub 130 prior to and during needle retraction, respectfully. In FIG.

16A, patch pump 380 having a housing 312 with a top housing surface 354, angled side surface 355, and bottom surface 356 is shown. The top housing surface 354 contains an attachment aperture 352 which provides an angled passageway 358 through the housing 312 at an angle that is generally parallel to that of the angled side surface 355. Accordingly, in some embodiments the angled side surface 355 is oriented at an angle generally consistent with the cannula 388 or other subcutaneous element. The angled passageway 358 provides space for a needle 122 to pass through the housing 312 and a location for securing the patch pump 380 to the cylinder hub 130 of the insertion mechanism 300 until the needle 122 is retracted.

The angled passageway 358 begins to extend inward from the attachment aperture 352 in an angled manner with a smooth surface diameter. Partially into the angled passageway 358 an annular constriction 360 protrudes inward from the perimeter before the angled passageway 358 again widens to a section 362 of smooth diameter that houses a self-sealing septum 364. The angled passageway 358 is reduced to a final, narrow diameter passage 366 leading to the bottom housing surface 356, out of which cannula 388 extends in an angled manner from the housing 312.

In FIG. 16A, features of the cylinder hub 130, consisting of retention fingers 350 (also interchangeably and more specifically identified individually as 350a, 350b . . . etc. in the figures and description), extend into the angled passageway 358. In the embodiment shown, only a first retention finger 350a and a second retention finger 350b are present, surrounded by a central passageway 368. In other embodiments, a greater number of retention fingers 350 can be present which are radially surrounded by the central passageway 368 in a spaced-apart manner. The retention fingers 350 have a generally smooth inner surface 370 partially surrounding the central passageway 368 which is in adjacent contact with the surface of the needle 122 extending therethrough. The outer surface portion 372 of the retention fingers 350 is generally smooth for a distance as it extends from the cylinder hub 130 into the contoured angled passageway 358 of the housing 312. A recessed section 374 is present partway along the outer surface 372 as well as an outwardly extending tab 376 extends toward the passageway wall at or near the distal end of the retention finger 350. In the initial retained position, the retention fingers 350 are engaged within the angled passageway 358 such that the outwardly extending tab 376 is located in the wider section 362 of the angled passageway 358 beyond the annular constriction 360. In this position, the annular constriction 360 projects inwardly toward recessed section 374 of the retention finger 350. The retention fingers 350 are generally held in place when needle 122 extends through the central passageway 368 as the needle 122 interferes with the ability of the retention fingers 350 to flex inwardly so that the annular constriction 360 and outwardly extending tabs 376 interfere with movement past each other.

FIG. 16B shows the release of the patch pump 380 upon retraction of the needle 122. Once the needle 122 has carried out angled insertion into a patient to properly place cannula 388 into the desired location, the needle 122 is retracted through the cannula 388, self-sealing septum 364, and through the central passageway 368 between the retention fingers 350. As the needle 122 is withdrawn from the central passageway 368, the retention fingers 350 are free to flex inwardly into the space of the central passageway 368 so that the annular constriction 360 no longer interferes with movement of the tabs 376. Accordingly, the patch pump 380 is freely released from the retention fingers 350 and remains deployed on a patient. This release enables the remaining features of the insertion mechanism 300 to be separated from the patch pump 380. Medicament reaches the top end of the cannula 388 through a cavity, not shown, below self-sealing septum 364 that is in fluid communication with fluid reservoir 332.

Figure 17:
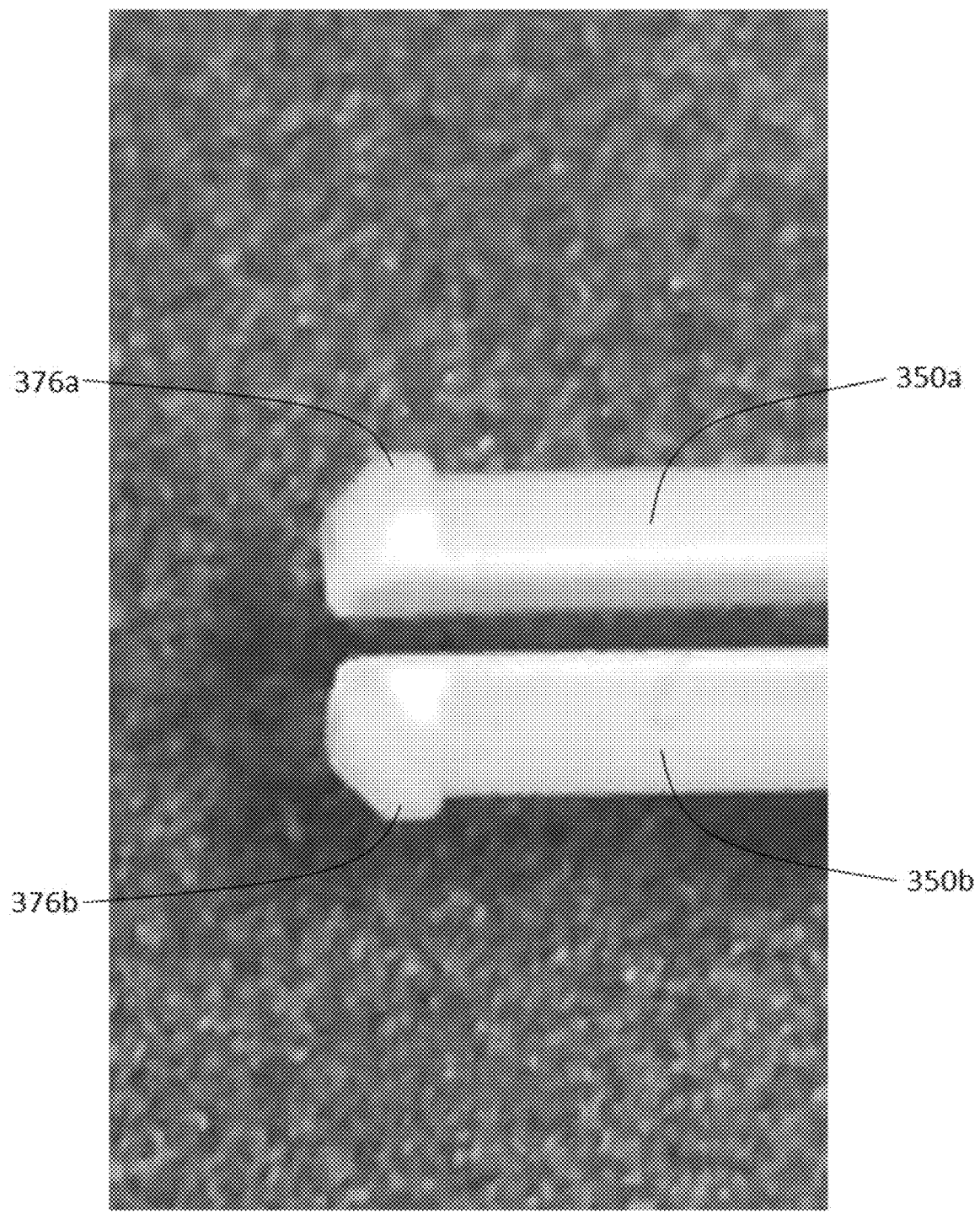
FIG. 17 is a perspective view depicting retention fingers located at the end portion of the cylinder hub according to an embodiment.

FIG. 17 is a perspective view depicting one embodiment of a pair of retention fingers 350a and 350b that could be used as part of the end portion 132 of the cylinder hub 130. Each retention finger 350a and 350b has a smooth inner surface and a projecting tab 376a and 376b extending outwardly at respective distal ends of the retention fingers 350a and 350b. The tab portion consists of a first projecting flat surface, a flat end surface, and an angled flat surface extending between the first projecting flat surface and the flat end surface. Various shapes and sizes may be used for tabs to provide secure engagement within the contoured passageway. In general, however, rigid outward extension of the tabs 376a and 376b are held in place and made possible based on interference of a central needle 122, when present, with the inside smooth surfaces of the retention fingers 350a and 350b.

It should also be appreciated that the exemplary embodiment or exemplary embodiments are only examples, and are not intended to limit the scope, applicability, or configuration of the invention in any way. Rather, the foregoing detailed description will provide those skilled in the art with an enabling disclosure for implementing the exemplary embodiment or exemplary embodiments. It should be understood that various changes can be made in the function and arrangement of elements without departing from the scope of the subject matter hereof as set forth in the appended claims and the legal equivalents thereof.

The embodiments above are intended to be illustrative and not limiting. Additional embodiments are within the claims. Although subject matter hereof has been described with reference to particular embodiments, workers skilled in the art will recognize that changes may be made in form and detail without departing from the spirit and scope of the subject matter.

Various modifications to subject matter hereof may be apparent to one of skill in the art upon reading this disclosure. For example, persons of ordinary skill in the relevant art will recognize that the various features described for the different embodiments of the invention can be suitably combined, un-combined, and re-combined with other features, alone, or in different combinations, within the spirit of the subject matter. Likewise, the various features described above should all be regarded as example embodiments, rather than limitations to the scope or spirit of the subject matter. Therefore, the above is not contemplated to limit the scope of the subject matter.

For purposes of interpreting the claims, it is expressly intended that the provisions of 35 U.S.C. § 112(f) are not to be invoked unless the specific terms "means for" or "step for" are recited in a claim.

The invention claimed is:
1. An insertion device comprising:
a housing comprising a first end;
a sleeve slidably arranged at least partially in the housing;
a cylinder hub at least partially arranged in the sleeve and the housing and comprising a shoulder portion, a body portion and an end portion, the shoulder portion proximate to the first end of the housing;
a needle hub slidably arranged in the cylinder hub and comprising a needle; and a site comprising a patient-side surface, a central hub having a side aperture formed therein, a subcutaneous element coupled to the site at an angle greater than 0 degrees and less than 90 degrees with respect to the patient-side surface, and a septum having a longitudinal axis that is coaxial with a longitudinal septum axis of the central hub extending substantially orthogonally from the patient side surface, the site arranged within the housing such that the needle can pass through the side aperture of the central hub and pass through the septum at an oblique angle relative to the longitudinal septum axis, to enter the subcutaneous element at the oblique angle.

2. The insertion device of claim 1, wherein the angle of greater than 0 degrees and less than 90 degrees is between about 20 degrees and about 50 degrees.

3. The insertion device of claim 1, further comprising a cap removably coupled with the housing and a lock pin removably coupled between the cap and the housing.

4. The insertion device of claim 1, wherein the needle hub further comprises at least two tabs and the sleeve comprises at least one rib.

5. The insertion device of claim 4, wherein the cylinder hub comprises at least two apertures, and wherein the at least two tabs are configured to interact with the at least two apertures, respectively.

6. The insertion device of claim 4, further comprises a biasing element arranged between the at least two tabs and the at least one rib.

7. The insertion device of claim 6, wherein the needle hub further comprises a snap arm, the cylinder hub comprises an aperture, and the sleeve comprises a trigger rib, and wherein the snap arm is configured to be released from the aperture by the trigger rib in operation of the insertion device.

8. The insertion device of claim 7, wherein the needle hub and the needle are configured to be retracted within the cylinder hub by the biasing element when the snap arm is released from the aperture by the trigger rib.

9. The insertion device of claim 1, wherein the subcutaneous element comprises a cannula.

10. The insertion device of claim 1, wherein the septum is arranged in the central hub and the needle passes through the central hub and the septum to enter the subcutaneous element at the angle.

11. The insertion device of claim 10, wherein the septum and the subcutaneous element are in fluid communication with one another.

12. The insertion device of claim 1, wherein the site comprises a patch pump.

13. The insertion device of claim 12, wherein the patch pump is selectively secured to the cylinder hub by a plurality of retention fingers with one or more tabs that are outwardly biased by the needle due to the position of the needle between the plurality of retention fingers.

14. The insertion device of claim 1, wherein the side aperture of the central hub can be used for attachment of a set buckle to the site after placement onto the skin of a patient.

15. A method comprising:
providing an insertion device comprising
a housing comprising a first end,
a sleeve slidably arranged at least partially in the housing,
a cylinder hub at least partially arranged in the sleeve and the housing and comprising a shoulder portion, a body portion and an end portion, the shoulder portion proximate to the first end of the housing, and
a needle hub slidably arranged in the cylinder hub and comprising a needle;
providing a site to be applied by the insertion device, the site comprising a patient-side surface, a central hub having a side aperture formed therein, a subcutaneous element to be inserted by the insertion device, the subcutaneous element coupled to the site at an angle greater than 0 degrees and less than 90 degrees with respect to the patient-side surface, and a septum having a longitudinal axis that is coaxial with a longitudinal septum axis extending substantially orthogonally from the patient side surface; and
configuring the insertion device and the site to be coupled with one another such that the needle can pass through the side aperture of the central hub and pass through the septum at an oblique angle relative to the longitudinal septum axis, to enter the subcutaneous element at the oblique angle to insert the subcutaneous element during use.

16. The method of claim 15, wherein the angle of greater than 0 degrees and less than 90 degrees is between about 20 degrees and about 50 degrees.

17. The method of claim 15, wherein the side aperture of the central hub can be used for attachment of a set buckle to the site after placement onto the skin of a patient.

18. An insertion device comprising:
a housing comprising a first end;
a sleeve slidably arranged at least partially in the housing;
a cylinder hub at least partially arranged in the sleeve and the housing and comprising a shoulder portion, a body portion and an end portion, the shoulder portion proximate to the first end of the housing; and
a needle hub slidably arranged in the cylinder hub and comprising a needle;
wherein the insertion device is configured to be coupled with a site to insert a subcutaneous element of the site subcutaneously, the subcutaneous element coupled to the site at an angle greater than 0 degrees and less than 90 degrees with respect to a patient-contacting surface of the site, the subcutaneous element secured in place with a septum having a longitudinal septum axis extending substantially orthogonally from the patient-contacting surface, the site coupled with the insertion device such that the needle can pass through at least a side aperture formed in a central hub of the site and pass through the septum at an oblique angle relative to the longitudinal septum axis, to enter the subcutaneous element at the oblique angle.

19. The insertion device of claim 18, wherein the angle of greater than 0 degrees and less than 90 degrees is between about 20 degrees to about 50 degrees.

20. The insertion device of claim 18, wherein the site comprises a sensor.

21. The insertion device of claim 18, wherein the site comprises a patch pump.

* * * * *